United States Patent
Shakhov et al.

(10) Patent No.: US 8,524,668 B2
(45) Date of Patent: Sep. 3, 2013

(54) METHODS OF PROTECTING AGAINST APOPTOSIS USING LIPOPEPTIDES

(75) Inventors: Alexander Shakhov, Orchard Park, NY (US); Andrei Gudkov, East Aurora, NY (US)

(73) Assignees: Cleveland Clinic Foundation, Cleveland, OH (US); Cleveland Biolabs, Inc., Buffalo, NY (US)

( * ) Notice: Subject to any disclaimer, the term of this patent is extended or adjusted under 35 U.S.C. 154(b) by 0 days.

(21) Appl. No.: 13/051,549

(22) Filed: Mar. 18, 2011

(65) Prior Publication Data

US 2011/0237507 A1 Sep. 29, 2011

Related U.S. Application Data

(62) Division of application No. 11/917,494, filed as application No. PCT/US2006/022865 on Jun. 13, 2006, now Pat. No. 8,008,260.

(60) Provisional application No. 60/689,810, filed on Jun. 13, 2005.

(51) Int. Cl.
*A61K 38/08* (2006.01)
*C07K 7/06* (2006.01)

(52) U.S. Cl.
USPC ........ 514/18.9; 514/19.3; 514/21.8; 530/330; 530/345

(58) Field of Classification Search
None
See application file for complete search history.

(56) References Cited

U.S. PATENT DOCUMENTS

| | | | |
|---|---|---|---|
| 5,449,761 A | 9/1995 | Belinka et al. | |
| 5,478,808 A | 12/1995 | Tanida et al. | |
| 5,478,809 A | 12/1995 | Tanida et al. | |
| 8,008,260 B2 * | 8/2011 | Shakhov et al. | 514/18.9 |
| 2003/0022867 A1 | 1/2003 | Stogniew et al. | |
| 2003/0170249 A1 | 9/2003 | Hakomori et al. | |
| 2004/0127405 A1 | 7/2004 | Muhlradt et al. | |
| 2004/0146552 A1 | 7/2004 | Spitler et al. | |
| 2004/0265231 A1 | 12/2004 | Blumenthal et al. | |
| 2005/0163764 A1 * | 7/2005 | Medzhitov et al. | 424/93.45 |
| 2006/0039895 A1 * | 2/2006 | Chute | 424/93.7 |

FOREIGN PATENT DOCUMENTS

| WO | 95/12675 | 5/1995 |
|---|---|---|
| WO | WO 2005057218 A2 * | 6/2005 |

OTHER PUBLICATIONS

Takeuchi et al. Discrimination of bacterial lipoproteins by Toll-like receptor 6. International Immunology. 2001, vol. 13, No. 7, pp. 933-940.*
Nagai, Yoshinori, et al., Toll-Like Receptors on Hematopoietic Progenitor Cells Stimulate Innate Immune System Replenishment, Immunity, Jun. 2006; 24(6): 801-812.
Ueda, Yoshihiro, et al., Inflammation Controls B Lymphopoiesis by Regulating Chemokine CXCL12 Expression, Journal of Experimental Medicine, 2004; 199(1): 47-57.
Sacht et al., Activation of nuclear factor-chi B in macrophages by mycoplasmal lipopeptides. European Journal of Immunology. 1998, vol. 28, pp. 4207-4212.

(Continued)

*Primary Examiner* — Jeffrey E Russel

(57) ABSTRACT

The use of lipopeptides as inducers of NF-κB for the protection of mammals from the effects of apoptosis is described.

14 Claims, 35 Drawing Sheets

(56) References Cited

OTHER PUBLICATIONS

Shinohara et al., Prevention of intestinal toxic effects and intensification of irinotecan's therapeutic efficacy against murine colon cancer liver metastases by oral administration of the lipopeptide JBT 3002. Clinical Cancer Research. Sep. 1998, vol. 4, pp. 2053-2063.

Souvannavong et al., Effect of synthetic lipids on apoptosis and expression of alkaline phosphatase in B-lymphocytes; influence on lipopolysaccharide action. FEMS Immunology and Medical Microbiology. 1999, vol. 26, pp. 37-47.

Muhlradt, et al., Isolation, Structure Elucidation, and Synthesis of a Macrophage Stimulatory Lipopeptide . . . Journal of Experimental Medicine. Jun. 2, 1997, vol. 185, No. 1, pp. 1951-1958.

Schneider, et al., Tumour suppresion induced by the macrophage activating lipopeptide Malp-2 . . . Gut. Mar. 2004, vol. 53, pp. 355-361.

Singh Vk et al., "Radioprotection by N-palmitoylated nonapeptide of human interleukin-1 beta", Peptides, 26(3), pp. 413-418, Mar. 2005.

* cited by examiner

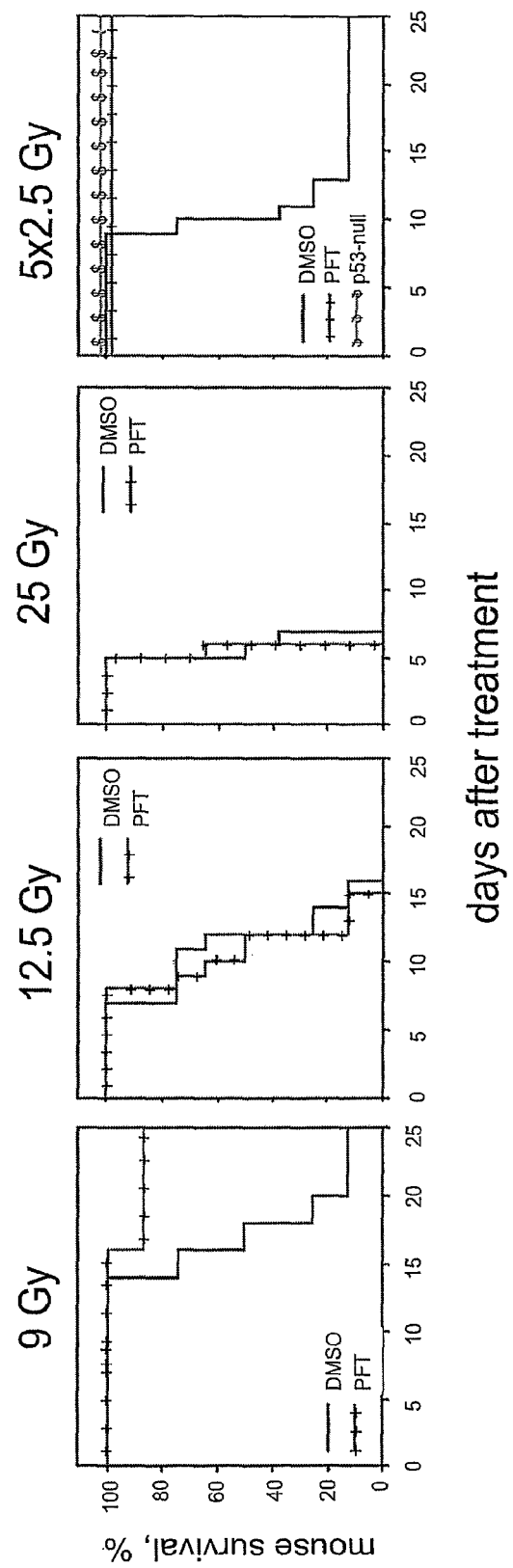

SEQUENCE LISTING

<160> NUMBER OF SEQ ID NOS: 52

<210> SEQ ID NO 1
<211> LENGTH: 4
<212> TYPE: PRT
<213> ORGANISM: Artificial
<220> FEATURE:
<223> OTHER INFORMATION: SYNTHETIC PEPTIDE

<400> SEQUENCE: 1

Ser Asn Asn Ala
1

<210> SEQ ID NO 2
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 2

Gly Ser Ser His His
1               5

<210> SEQ ID NO 3
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 3

Lys Gln Asn Val Ser
1               5

```
<210> SEQ ID NO 4
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 4

Asn Asn Ser Gly Lys
1               5

<210> SEQ ID NO 5
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 5

Gln Pro Asp Arg Tyr
1               5

<210> SEQ ID NO 6
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 6

Arg Pro Asp Arg Tyr
1               5

<210> SEQ ID NO 7
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 7

Ser Glu Glu Glu Glu
1               5

<210> SEQ ID NO 8
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 8

Ser Lys Lys Lys Lys
1               5

<210> SEQ ID NO 9
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 9

Ser Asn Asn Asn Ala
1               5
```

```
<210> SEQ ID NO 10
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 10

Ser Pro Pro Pro Pro
1               5

<210> SEQ ID NO 11
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 11

Gly Gln His His Met
1               5

<210> SEQ ID NO 12
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 12

Gly Gln His His His
1               5

<210> SEQ ID NO 13
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 13

Ser Ser His His Met
1               5

<210> SEQ ID NO 14
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 14

Gly Ser His His Met
1               5

<210> SEQ ID NO 15
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 15

Ser Gln Met His His
1               5

<210> SEQ ID NO 16
<211> LENGTH: 5
```

```
<212> TYPE: PRT
<213> ORGANISM: Artificial
<220> FEATURE:
<223> OTHER INFORMATION: SYNTHETIC PEPTIDE

<400> SEQUENCE: 16

Gly Glu Thr Asp Lys
1               5

<210> SEQ ID NO 17
<211> LENGTH: 5
<212> TYPE: PRT
<213> ORGANISM: Artificial
<220> FEATURE:
<223> OTHER INFORMATION: SYNTHETIC PEPTIDE

<400> SEQUENCE: 17

Gly Glu Glu Ser Asn
1               5

<210> SEQ ID NO 18
<211> LENGTH: 5
<212> TYPE: PRT
<213> ORGANISM: Artificial
<220> FEATURE:
<223> OTHER INFORMATION: SYNETHIC PEPTIDE

<400> SEQUENCE: 18

Gly Glu Glu Asp Asp
1               5

<210> SEQ ID NO 19
<211> LENGTH: 6
<212> TYPE: PRT
<213> ORGANISM: Artificial
<220> FEATURE:
<223> OTHER INFORMATION: SYNTHETIC PEPTIDE

<400> SEQUENCE: 19

Thr Glu Asn Val Lys Glu
1               5

<210> SEQ ID NO 20
<211> LENGTH: 8
<212> TYPE: PRT
<213> ORGANISM: Artificial
<220> FEATURE:
<223> OTHER INFORMATION: SYNTHETIC PEPTIDE

<400> SEQUENCE: 20

Gln Gly Glu Glu Ser Asn Asp Lys
1               5

<210> SEQ ID NO 21
<211> LENGTH: 9
<212> TYPE: PRT
<213> ORGANISM: Artificial
<220> FEATURE:
<223> OTHER INFORMATION: SYNTHETIC PEPTIDE

<400> SEQUENCE: 21

Val Gln Gly Glu Glu Ser Asn Asp Lys
1               5

<210> SEQ ID NO 22
<211> LENGTH: 9
<212> TYPE: PRT
<213> ORGANISM: Artificial
```

```
<220> FEATURE:
<223> OTHER INFORMATION: SYNTHETIC PEPTIDE

<400> SEQUENCE: 22

Phe Glu Pro Pro Pro Ala Thr Thr Thr
1               5

<210> SEQ ID NO 23
<211> LENGTH: 9
<212> TYPE: PRT
<213> ORGANISM: Artificial
<220> FEATURE:
<223> OTHER INFORMATION: SYNTHETIC PEPTIDE

<400> SEQUENCE: 23

Gly Asp Lys Tyr Phe Lys Glu Thr Glu
1               5

<210> SEQ ID NO 24
<211> LENGTH: 9
<212> TYPE: PRT
<213> ORGANISM: Artificial
<220> FEATURE:
<223> OTHER INFORMATION: SYNTHETIC PEPTIDE

<400> SEQUENCE: 24

Gly Asp Pro Lys His Pro Lys Ser Phe
1               5

<210> SEQ ID NO 25
<211> LENGTH: 9
<212> TYPE: PRT
<213> ORGANISM: Artificial
<220> FEATURE:
<223> OTHER INFORMATION: SYNTHETIC PEPTIDE

<400> SEQUENCE: 25

Gly Gly Gln Glu Lys Ser Ala Ala Gly
1               5

<210> SEQ ID NO 26
<211> LENGTH: 9
<212> TYPE: PRT
<213> ORGANISM: Artificial
<220> FEATURE:
<223> OTHER INFORMATION: SYTHETIC PEPTIDE

<400> SEQUENCE: 26

Gly Pro Cys Pro Gly Cys Pro Pro Cys
1               5

<210> SEQ ID NO 27
<211> LENGTH: 9
<212> TYPE: PRT
<213> ORGANISM: Artificial
<220> FEATURE:
<223> OTHER INFORMATION: SYNTHETIC PEPTIDE

<400> SEQUENCE: 27

Pro Pro Cys Pro Gly Cys Pro Pro Cys
1               5

<210> SEQ ID NO 28
<211> LENGTH: 11
<212> TYPE: PRT
<213> ORGANISM: Artificial
<220> FEATURE:
<223> OTHER INFORMATION: SYNTHETIC PEPTIDE
```

<400> SEQUENCE: 28

Asp Asn Glu Glu Lys Pro Thr Pro Glu Gln Asp
1               5                   10

<210> SEQ ID NO 29
<211> LENGTH: 11
<212> TYPE: PRT
<213> ORGANISM: Artificial
<220> FEATURE:
<223> OTHER INFORMATION: SYNTHETIC PEPTIDE

<400> SEQUENCE: 29

Gly Asn Gly Gly Ala Pro Ala Gln Pro Lys Gly
1               5                   10

<210> SEQ ID NO 30
<211> LENGTH: 12
<212> TYPE: PRT
<213> ORGANISM: Artificial
<220> FEATURE:
<223> OTHER INFORMATION: SYNTHETIC PEPTIDE

<400> SEQUENCE: 30

Phe Glu Pro Pro Pro Ala Thr Thr Thr Lys Ser Lys
1               5                   10

<210> SEQ ID NO 31
<211> LENGTH: 13
<212> TYPE: PRT
<213> ORGANISM: Artificial
<220> FEATURE:
<223> OTHER INFORMATION: SYNTHETIC PEPTIDE

<400> SEQUENCE: 31

Gly Asn Asn Asp Glu Ser Asn Ile Ser Phe Lys Glu Lys
1               5                   10

<210> SEQ ID NO 32
<211> LENGTH: 14
<212> TYPE: PRT
<213> ORGANISM: Artificial
<220> FEATURE:
<223> OTHER INFORMATION: SYNTHETIC PEPTIDE

<400> SEQUENCE: 32

Gly Asp Pro Lys His Pro Lys Ser Phe Thr Gly Trp Val Ala
1               5                   10

<210> SEQ ID NO 33
<211> LENGTH: 15
<212> TYPE: PRT
<213> ORGANISM: Artificial
<220> FEATURE:
<223> OTHER INFORMATION: SYNTHETIC PEPTIDE

<400> SEQUENCE: 33

Ala Gln Asn Pro Asn Lys Thr Asn Ser Asn Leu Asp Ser Ser Lys
1               5                   10                  15

<210> SEQ ID NO 34
<211> LENGTH: 15
<212> TYPE: PRT
<213> ORGANISM: Artificial
<220> FEATURE:
<223> OTHER INFORMATION: SYNTHETIC PEPTIDE

<400> SEQUENCE: 34

Asn Lys Asp Asn Glu Ala Glu Pro Val Thr Glu Gly Asn Ala Thr
1               5                   10                  15

<210> SEQ ID NO 35
<211> LENGTH: 15
<212> TYPE: PRT
<213> ORGANISM: Artificial
<220> FEATURE:
<223> OTHER INFORMATION: SYNTHETIC PEPTIDE

<400> SEQUENCE: 35

Ser Lys Glu Gly Asn Gly Pro Asp Pro Asp Asn Ala Ala Lys Ser
1               5                   10                  15

<210> SEQ ID NO 36
<211> LENGTH: 16
<212> TYPE: PRT
<213> ORGANISM: Artificial
<220> FEATURE:
<223> OTHER INFORMATION: SYNTHETIC PEPTIDE

<400> SEQUENCE: 36

Gly Asp Lys Thr Pro Ser Thr Lys Ser Ala Gly Lys Val Glu Asn Lys
1               5                   10                  15

<210> SEQ ID NO 37
<211> LENGTH: 17
<212> TYPE: PRT
<213> ORGANISM: Artificial
<220> FEATURE:
<223> OTHER INFORMATION: SYNTHETIC PEPTIDE

<400> SEQUENCE: 37

Gly Glu Thr Asp Lys Glu Gly Lys Ile Ile Arg Ile Phe Asp Asn Ser
1               5                   10                  15
Phe

<210> SEQ ID NO 38
<211> LENGTH: 17
<212> TYPE: PRT
<213> ORGANISM: Artificial
<220> FEATURE:
<223> OTHER INFORMATION: SYNTHETIC PEPTIDE

<400> SEQUENCE: 38

Ser Ser Thr Ser Glu Asn Asn Gly Asn Gly Asn Gly Asn Gly Gly Thr
1               5                   10                  15
Asp

<210> SEQ ID NO 39
<211> LENGTH: 18
<212> TYPE: PRT
<213> ORGANISM: Artificial
<220> FEATURE:
<223> OTHER INFORMATION: SYNTHETIC PEPTIDE

<400> SEQUENCE: 39

Gly Asn Asn Asp Glu Ser Asn Ile Ser Phe Lys Glu Lys Ser Glu Glu
1               5                   10                  15
Glu Glu

<210> SEQ ID NO 40
<211> LENGTH: 18
<212> TYPE: PRT
<213> ORGANISM: Artificial

```
<220> FEATURE:
<223> OTHER INFORMATION: SYNTHETIC PEPTIDE

<400> SEQUENCE: 40

Gly Asn Asn Asp Glu Ser Asn Ile Ser Phe Lys Glu Lys Ser Lys Lys
1               5                   10                  15

Lys Lys

<210> SEQ ID NO 41
<211> LENGTH: 18
<212> TYPE: PRT
<213> ORGANISM: Artificial
<220> FEATURE:
<223> OTHER INFORMATION: SYNTHETIC PEPTIDE

<400> SEQUENCE: 41

Gly Asn Asn Asp Glu Ser Asn Ile Ser Phe Lys Glu Lys Ser Pro Pro
1               5                   10                  15

Pro Pro

<210> SEQ ID NO 42
<211> LENGTH: 18
<212> TYPE: PRT
<213> ORGANISM: Artificial
<220> FEATURE:
<223> OTHER INFORMATION: SYNTHETIC PEPTIDE

<400> SEQUENCE: 42

Ser Ser Asn Lys Ser Thr Thr Gly Ser Gly Glu Thr Thr Thr Ala Ala
1               5                   10                  15

Gly Thr

<210> SEQ ID NO 43
<211> LENGTH: 19
<212> TYPE: PRT
<213> ORGANISM: Artificial
<220> FEATURE:
<223> OTHER INFORMATION: SYNTHETIC PEPTIDE

<400> SEQUENCE: 43

Cys Gly Asn Asn Asp Glu Ser Asn Ile Ser Phe Lys Glu Lys Ser Lys
1               5                   10                  15

Lys Lys Lys

<210> SEQ ID NO 44
<211> LENGTH: 19
<212> TYPE: PRT
<213> ORGANISM: Artificial
<220> FEATURE:
<223> OTHER INFORMATION: SYNTHETIC PEPTIDE

<400> SEQUENCE: 44

Gly Ser Pro Leu Ser Phe Glu Ser Ser Val Gln Leu Ile Val Ser Asp
1               5                   10                  15

Asn Ser Ser

<210> SEQ ID NO 45
<211> LENGTH: 19
<212> TYPE: PRT
<213> ORGANISM: Artificial
<220> FEATURE:
<223> OTHER INFORMATION: SYNTHETIC PEPTIDE

<400> SEQUENCE: 45
```

```
Ser Asn Tyr Ala Lys Lys Val Val Lys Gln Lys Asn His Val Tyr Thr
1               5                   10                  15

Pro Val Tyr

<210> SEQ ID NO 46
<211> LENGTH: 21
<212> TYPE: PRT
<213> ORGANISM: Artificial
<220> FEATURE:
<223> OTHER INFORMATION: SYNTHETIC PEPTIDE

<400> SEQUENCE: 46

Ala Asp Val Ile Ala Lys Ile Val Glu Ile Val Lys Gly Leu Ile Asp
1               5                   10                  15

Gln Phe Thr Gln Lys
            20

<210> SEQ ID NO 47
<211> LENGTH: 21
<212> TYPE: PRT
<213> ORGANISM: Artificial
<220> FEATURE:
<223> OTHER INFORMATION: SYNTHETIC PEPTIDE

<400> SEQUENCE: 47

Gly Ala Ala Ser Ser Leu Thr Tyr Glu Ser Ser Val Gln Leu Val Val
1               5                   10                  15

Ser Asp Asn Ser Ser
            20

<210> SEQ ID NO 48
<211> LENGTH: 21
<212> TYPE: PRT
<213> ORGANISM: Artificial
<220> FEATURE:
<223> OTHER INFORMATION: SYNTHETIC PEPTIDE

<400> SEQUENCE: 48

Gly Gly Glu Pro Ala Ala Gln Ala Pro Ala Glu Thr Pro Ala Ala Ala
1               5                   10                  15

Ala Glu Ala Ala Ser
            20

<210> SEQ ID NO 49
<211> LENGTH: 20
<212> TYPE: PRT
<213> ORGANISM: Artificial
<220> FEATURE:
<223> OTHER INFORMATION: SYNTHETIC PEPTIDE

<400> SEQUENCE: 49

Gly Gln Thr Asp Asn Asn Ser Ser Gln Ser Gln Gln Pro Gly Ser Gly
1               5                   10                  15

Thr Thr Asn Thr
            20

<210> SEQ ID NO 50
<211> LENGTH: 22
<212> TYPE: PRT
<213> ORGANISM: Artificial
<220> FEATURE:
<223> OTHER INFORMATION: SYNTHETIC PEPTIDE

<400> SEQUENCE: 50

Ser Gly Ala Leu Ala Ala Thr Ser Asp Asp Asp Val Lys Lys Ala Ala
```

```
                1               5                   10                  15
Thr Val Ala Ile Val Ala
                20

<210> SEQ ID NO 51
<211> LENGTH: 22
<212> TYPE: PRT
<213> ORGANISM: Artificial
<220> FEATURE:
<223> OTHER INFORMATION: SYNTHETIC PEPTIDE

<400> SEQUENCE: 51

Ser Ile Val Ser Thr Ile Ile Glu Val Val Lys Thr Ile Val Asp Ile
1               5                   10                  15

Val Lys Lys Phe Lys Lys
                20

<210> SEQ ID NO 52
<211> LENGTH: 22
<212> TYPE: PRT
<213> ORGANISM: Artificial
<220> FEATURE:
<223> OTHER INFORMATION: SYNTHETIC PEPTIDE

<400> SEQUENCE: 52

Ser Ser Gly Gly Gly Gly Val Ala Ala Asp Ile Gly Ala Gly Leu Ala
1               5                   10                  15

Asp Ala Leu Thr Ala Pro
                20
```

METHODS OF PROTECTING AGAINST APOPTOSIS USING LIPOPEPTIDES

CROSS-REFERENCE TO RELATED APPLICATIONS

This is a divisional of U.S. patent application Ser. No. 11/917,494, filed Jul. 21, 2008, now U.S. Pat. No. 8,008,260 which is the national stage of International Application No. PCT/US2006/022865, filed Jun. 13, 2006, which claims the benefit of U.S. Provisional Patent Application No. 60/689,810 filed Jun. 13, 2005, the contents of all of which are incorporated herein by reference.

FIELD OF THE INVENTION

This invention relates to the use of inducers of NF-κB to protect mammals from the effects of apoptosis. More specifically, this invention relates to the use of inducers of NF-κB to protect mammals from exposure to stress, such as radiation and cancer treatments.

BACKGROUND OF THE INVENTION

The progression from normal cells to tumor cells involves a loss of negative mechanisms of growth regulation, including resistance to growth inhibitory stimuli and a lack of dependence on growth factors and hormones. Traditional cancer treatments that are based on radiation or cytotoxic drugs rely on the differences in growth control of normal and malignant cells. Traditional cancer treatments subject cells to severe genotoxic stress. Under these conditions, the majority of normal cells become arrested and therefore saved, while tumor cells continues to divide and die.

However, the nature of conventional cancer treatment strategies is such that normal rapidly dividing or apoptosis-prone tissues are at risk. Damage to these normal rapidly dividing cells causes the well-known side effects of cancer treatment (sensitive tissues: hematopoiesis, small intestine, hair follicles). The natural sensitivity of such tissues is complicated by the fact that cancer cells frequently acquire defects in suicidal (apoptotic) machinery and therapeutic procedures that cause death in normal sensitive tissues may not be effective on cancer cells. Conventional attempts to minimize the side effects of cancer therapies are based on (a) making tumor cells more susceptible to treatment, (b) making cancer therapies more specific for tumor cells, or (c) promoting regeneration of normal tissue after treatment (e.g., erythropoietin, GM-CSF, and KGF). Each of these, however, has limited effectiveness. As a result, there continues to be a need for therapeutic agents to mitigate the side effects associated with chemotherapy and radiation therapy in the treatment of cancer. This invention fulfills these needs and provides other related advantages.

SUMMARY OF THE INVENTION

Provided herein is a method of protecting a mammal from one or more conditions or treatments that trigger apoptosis. A mammal may be administered a composition comprising a pharmaceutically acceptable amount of a compound of the formula:

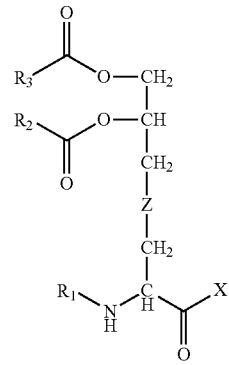

wherein,
$R_1$ represents H or —CO—$R_4$,
$R_2$, $R_3$ and $R_4$ independently are H or optionally substituted $C_8$-$C_{16}$ aliphatic;
X is a peptide; and
Z is S or $CH_2$.

The peptide may comprise a sequence set forth in SEQ ID NOs: 1-52. The first five amino acids of the peptide may be chosen from the amino acids at the positions referred to in Table 2. The compound may be an RR or RS stereoisomer, or mixture thereof. The compound may also be of the formula:

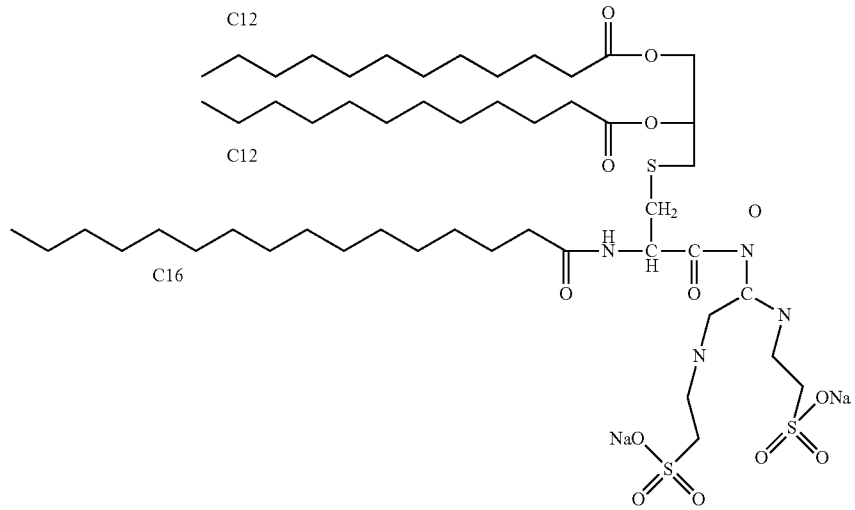

The condition that triggers apoptosis may be radiation, wounding, poisoning, infection or temperature shock. The treatment that triggers apoptosis may be a cancer treatment. The cancer treatment may be chemotherapy or radiation therapy. The tissue wherein apoptosis is triggered may be the spleen, thymus, GI tract, lungs, kidneys, liver, cardiovascular system, blood vessel endothelium, nervous system (central or peripheral), hematopoietic progenitor cells (bone marrow), immune system, hair follicles, or the reproductive system.

The compound may be administered in combination with a radioprotectant. The radioprotectant may be an antioxidant, such as amifostine or vitamine E. The radioprotectant may also be a cytokine, such as stem cell factor. The radioprotectant may also be flagellin, latent TGFβ, or an activator of a TLR.

BRIEF DESCRIPTION OF THE DRAWINGS

FIG. 1 illustrates that p53 deficiency accelerated the development of radiation-induced gastrointestinal syndrome in mice. FIG. 1a presents graphs of the percent survival of mice exposed to 9, 12.5, 25, or 5×2.5 Gy of total body gamma radiation following pretreatment with an inhibitor of p53, pifithrin-alpha (PFT), or DMSO (control). p53-null mice were also exposed to the fractioned cumulative radiation dose of 12.5 Gy (5×2.5 Gy).

FIG. 2 illustrates the dynamics of cell proliferation and survival in the small intestines of wild type and p53-null mice. FIG. 2a (right) shows photomicrographs of BrdU incorporation in the small intestine of wild type and p53-null mice at different time points after 15 Gy of gamma radiation. Regions of the 96 h images are shown at higher magnification.

FIG. 5 illustrates the determination of the optimal time for intraperitoneal injection of CBLB601.

FIG. 6 illustrates the determination of the optimal dose of CBLB601.

FIG. 7 illustrates the determination of the dose of radiation protected by CBLB601.

FIG. 12 illustrates the determination of the optimal time for intramuscular injection of CBLB601.

FIG. 16 depicts the immune responses of CNLB601-treated mice that were immunized with flagellin 8, 18, or 20 weeks after irradiation.

FIG. 18 presents the activation of a NF-κB reporter by various CBLB compounds in 293 cells expressing the TLR2/TLR6 heterodimer.

DETAILED DESCRIPTION

Figure 1B:
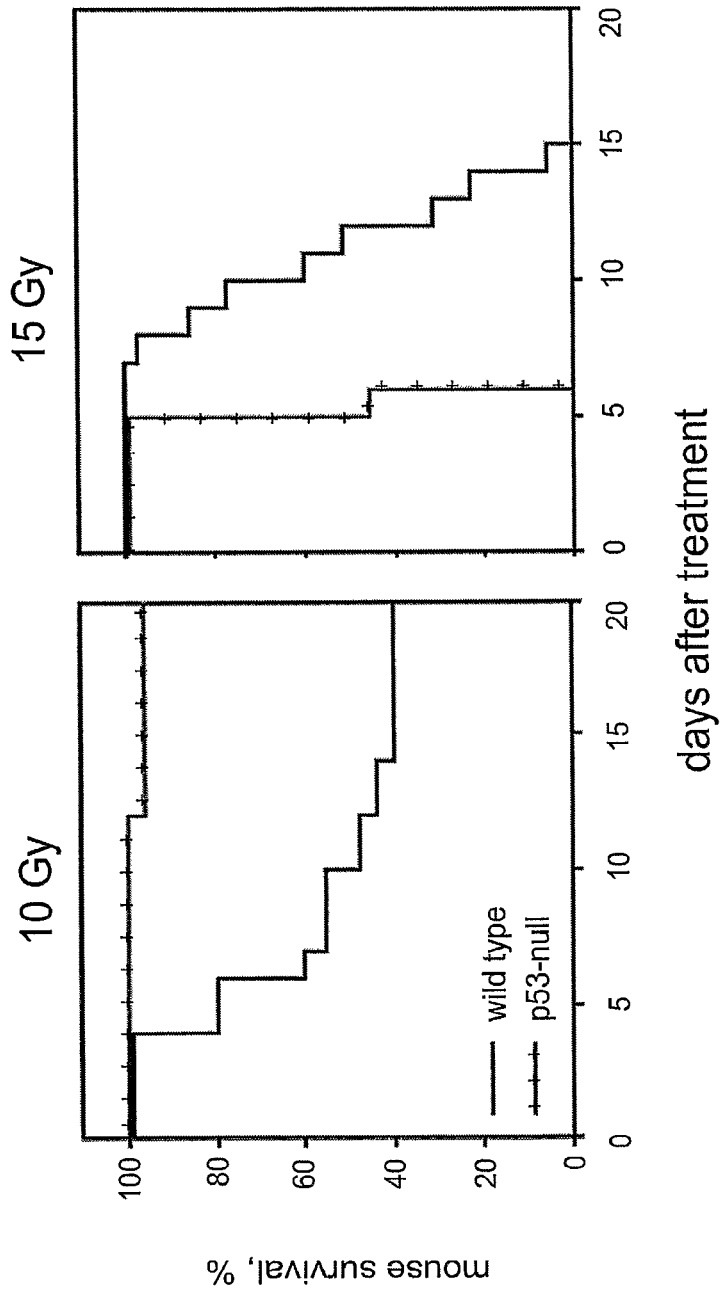
FIG. 1b presents graphs of the percent survival of wild type and p53-null mice after exposure to low (10 Gy) or high (15 Gy) doses of total body gamma radiation.

Provided herein is a method of protecting normal cells and tissues from apoptosis caused by a variety of stresses. Apoptosis normally functions to "clean" tissues from wounded or genetically damaged cells, while cytokines mobilize the defense system of the organism against the stress. However, under conditions of severe injury, both stress response mechanisms can by themselves act as causes of death. For example, lethality from radiation may result from massive apoptosis occurring in hematopoietic, immune and digestive systems.

There are two major mechanisms controlling apoptosis in the cell: the p53 (pro-apoptotic) and the NF-κB pathway (anti-apoptotic). Both pathways are frequently deregulated in tumors: p53 may be lost, while NF-κB may become constitutively active. Hence, inhibition of p53 and/or activation of NF-κB in normal cells may protect them from death caused by stresses. Such an approach in cancer treatments would not make tumor cells more resistant to treatment because they may already have these control mechanisms deregulated. This contradicts the conventional view on p53 and NF-κB, which are considered as targets for activation and repression, respectively.

As described herein, NF-κB activity may be induced to protect normal cells from apoptosis. By inducing NF-κB activity in a mammal, normal cells may be protected from apoptosis attributable to cellular stress. Once the normal cells recover from the stress, NF-κB activity may be restored to normal levels. By temporarily inducing NF-κB activity, cells may be protected from a variety of stresses. This may provide control of both inflammatory responses and the life-death decisions of cells from injured tissues and organs.

The protective role of NF-κB may be mediated by transcriptional activation of multiple genes coding for: a) anti-apoptotic proteins that block both major apoptotic pathways, b) cytokines and growth factors that induce proliferation and survival of hematopoietic and other stem cells, and c) potent ROS-scavenging antioxidant proteins, such as MnSOD (SOD-2). Thus, for example, by transient activation of NF-κB for radioprotection, it may be possible to achieve not only suppression of apoptosis in cancer patients, but also the ability to reduce the rate of secondary cancer incidence because of its simultaneous immunostimulatory effects, which, may be achieved if activation of NF-κB is mediated by Toll-like receptors.

Another attractive property of the NF-κB pathway as a target is its activation by numerous natural factors. Among these, are multiple pathogen-associated molecular patterns (PAMPs). PAMPs are present only in microorganisms and are not found in the host organism, are characteristic for large groups of pathogens, and cannot be easily mutated. They are recognized by Toll-like receptors (TLRs), the key sensor elements of innate immunity. TLRs act as a first warning mechanism of the immune system by inducing migration and activation of immune cells directly or through cytokine release. TLRs are type I membrane proteins, known to work as homo- and heterodimers. Upon ligand binding, TLRs recruit MyD88 protein, an indispensable signaling adaptor for most TLRs. The signaling cascade that follows leads to effects including (i) activation of NF-κB pathway, and (ii) activation of MAPKs, including Jun N-terminal kinase (JNK). Unlike cytokines, many PAMPs have little effect besides activating TLRs, and thus, are unlikely to produce side effects. Moreover, numerous TLTs (TLR1-TLR10) are present in humans. Consistent with their function of immunocyte activation, all TLRs are expressed in spleen and peripheral blood leukocytes, with more TLR-specific patterns of expression in other lymphoid organs and subsets of leukocytes. All of the TLRs are also expressed in the endothelial and mucosal epithelial cells of the skin and the respiratory, intestinal, and genitourinary tracts.

1. Definitions

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "administer", when used to describe the dosage of an agent that induces NF-κB activity, means a single dose or multiple doses of the agent.

The term "aliphatic" as used herein refers to an unbranched, branched or cyclic hydrocarbon group, which may be substituted or unsubstituted, and which may be saturated or unsaturated, but which is not aromatic. The term aliphatic further includes aliphatic groups, which comprise oxygen, nitrogen, sulfur or phosphorous atoms replacing one or more carbons of the hydrocarbon backbone.

The term "alkyl" as used herein alone or in combination refers to a branched or unbranched, saturated aliphatic group. Representative examples of alkyl groups include, but are not limited to, methyl, ethyl, n-propyl, isopropyl, n-butyl, isobutyl, sec-butyl, tert-butyl, octyl, decyl, tetradecyl, hexadecyl, eicosyl, tetacosyl and the like.

The term "alkenyl" as used herein alone or in combination refers to a branched or unbranched, unsaturated aliphatic group containing at least one carbon-carbon double bond which may occur at any stable point along the chain. Representative examples of alkenyl groups include, but are not limited to, ethenyl, E- and Z-pentenyl, decenyl and the like.

The term "alkynyl" as used herein alone or in combination refers to a branched or unbranched, unsaturated aliphatic group containing at least one carbon-carbon triple bond which may occur at any stable point along the chain. Representative examples of alkynyl groups include, but are not limited to, ethynyl, propynyl, propargyl, butynyl, hexynyl, decynyl and the like.

The term "analog" when used in the context of a peptide or polypeptide, means a peptide or polypeptide comprising one or more non-standard amino acids or other structural variations from the conventional set of amino acids.

The term "antibody" as used herein means an antibody of classes IgG, IgM, IgA, IgD or IgE, or fragments or derivatives thereof, including Fab, F(ab')$_2$, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety.

The term "apoptosis" as used herein refers to a form of cell death that includes progressive contraction of cell volume with the preservation of the integrity of cytoplasmic organelles; condensation of chromatin (i.e., nuclear condensation), as viewed by light or electron microscopy; and/or DNA cleavage into nucleosome-sized fragments, as determined by centrifuged sedimentation assays. Cell death occurs when the membrane integrity of the cell is lost (e.g., membrane blebbing) with engulfment of intact cell fragments ("apoptotic bodies") by phagocytic cells.

The term "cancer" as used herein means any condition characterized by resistance to apoptotic stimuli.

The term "cancer treatment" as used herein means any treatment for cancer known in the art including, but not limited to, chemotherapy and radiation therapy.

The term "combination with" when used to describe administration of an agent that induces NF-κB activity and an additional treatment means that the agent may be administered prior to, together with, or after the additional treatment, or a combination thereof.

The term "derivative" when used in the context of a peptide or polypeptide, means a peptide or polypeptide different other than in primary structure (amino acids and amino acid analogs). By way of illustration, derivatives may differ by being glycosylated, one form of post-translational modification. For example, peptides or polypeptides may exhibit glycosylation patterns due to expression in heterologous systems. If at least one biological activity is retained, then these peptides or polypeptides are derivatives according to the invention. Other derivatives include, but are not limited to, fusion peptides or fusion polypeptides having a covalently modified N- or C-terminus, PEGylated peptides or polypeptides, peptides or polypeptides associated with lipid moieties, alkylated peptides or polypeptides, peptides or polypeptides linked via an amino acid side-chain functional group to other peptides, polypeptides or chemicals, and additional modifications as would be understood in the art.

The term "fragment" when used in the context of a peptide or polypeptide, may mean a peptide of from about 6 to about 10 amino acids in length. The fragment may be 6, 7, 8, 9 or 10 amino acids in length.

The term "homolog" when used in the context of a peptide or polypeptide, means a peptide or polypeptide sharing a common evolutionary ancestor.

The term "saturated" as used herein refers to a group where all available valence bonds of the backbone atoms are attached to other atoms.

The term "substituted" as used herein refers to a group having one or more hydrogens or other atoms removed from a carbon and replaced with a further group. Substituted groups herein may be substituted with one to five, or one to three substituents. Representative examples of such substituents include, but are not limited to aliphatic groups, aromatic groups, alkyl, alkenyl, alkynyl, aryl, alkoxy, halo, aryloxy, carbonyl, acryl, cyano, amino, nitro, phosphate-containing groups, sulfur-containing groups, hydroxyl, alkylcarbonyloxy, arylcarbonyloxy, alkoxycarbonyloxy, aryloxycarbonyloxy, alkylcarbonyl, arylcarbonyl, alkoxycarbonyl, aminocarbonyl, alkylaminocarbonyl, dialkylaminocarbonyl, alkylthiocarbonyl, acylamino, amidino, imino, alkylthio, arylthio, thiocarboxylate, alkylsulfinyl, trifluoromethyl, azido, heterocyclyl, alkylaryl, heteroaryl, semicarbazido, thiosemicarbazido, maleimido, oximino, imidate, cycloalkyl, cycloalkylcarbonyl, dialkylamino, arylcycloalkyl, arylcarbonyl, arylalkylcarbonyl, arylcycloalkylcarbonyl, arylphosphinyl, arylalkylphosphinyl, arylcycloalkylphosphinyl, arylphosphonyl, arylalkylphosphonyl, arylcycloalkylphosphonyl, arylsulfonyl, arylalkylsulfonyl, arylcycloalkylsulfonyl, combinations thereof, and substitutions thereto.

The term "treat" or "treating" when referring to protection of a mammal from a condition, means preventing, suppressing, repressing, or eliminating the condition. Preventing the condition involves administering a composition of this invention to a mammal prior to onset of the condition. Suppressing the condition involves administering a composition of this invention to a mammal after induction of the condition but before its clinical appearance. Repressing the condition involves administering a composition of this invention to a mammal after clinical appearance of the condition such that the condition is reduced or maintained. Elimination the condition involves administering a composition of this invention to a mammal after clinical appearance of the condition such that the mammal no longer suffers the condition.

The term "tumor cell" as used herein means any cell characterized by resistance to apoptotic stimuli.

The term "unsaturated" as used herein refers to a group where at least one available valence bond of two adjacent backbone atoms is not attached to other atoms.

The term "unsubstituted" as used herein refers to a group that does not have any further groups attached thereto or substituted therefor.

The term "variant" when used in the context of a peptide or polypeptide, means a peptide or polypeptide that differs in amino acid sequence by the insertion, deletion, or conservative substitution of amino acids, but retains at least one biological activity. For purposes of this invention, "biological activity" includes, but is not limited to, the ability to be bound by a specific antibody. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art (Kyte et al., J. Mol. Biol.

157:105-132, 1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated herein by reference. Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. Lipopeptides

A lipopeptide may be used as an agent to induce NF-κB activity. Lipopeptides are part of the outer membranes of Gram-negative bacteria, Gram-positive bacteria, and mycoplasma. Bacterial lipopeptides have no shared sequence homology, but are characterized by the unusual N-terminal amino acid S-(2,3-dihydroxypropyl)-L-cysteine that is acylated by two or three fatty acids. Bacterial lipopeptides are strong immune modulators that activate early host responses after infection by signaling through TLR2-TLR1 or TLR2-TLR6 heterodimers, leading to the activation of NF-κB and cytokine production. Synthetic analogues of the N-terminal lipopeptides of natural lipopeptides are potent activators of TLRs and NF-κB, as well as being immunoadjuvants in vivo and in vitro.

The lipopeptide may be a compound of the formula:

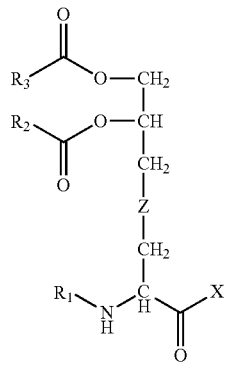

wherein,
$R_1$ represents H or —CO—$R_4$,
$R_2$, $R_3$ and $R_4$ independently are H or optionally substituted aliphatic;
X is H or a peptide; and
Z is S or $CH_2$.

The lipopeptide may comprise two or three fatty acids. The aliphatic substituents of $R_2$, $R_3$ and $R_4$ may comprise from 6 to 20 carbon atoms. $R_2$, $R_3$ and $R_4$ may be $C_6$-$C_{20}$ alkyl, $C_6$-$C_{20}$ alkenyl, or $C_6$-$C_{20}$ alkynyl. Representative examples of alkyl substituents at $R_2$, $R_3$ and $R_4$ include $C_6$, $C_8$, $C_9$, $C_{10}$, $C_{12}$, $C_{14}$, and $C_{16}$. Representative examples of alkenyl substituents at $R_2$, $R_3$ and $R_4$ include $C_{10:1}^{D1\ trans}$, $C_{18:1}^{D9}$, and $C_{18:2}^{D9,12}$.

The peptide may comprise between at least 4 or 5 amino acids and no more than 20, 30 or 40 amino acids. The peptide moiety may be essential for activity and the activity of the lipopeptide may by modulated by the amino acid sequence, but biological activity may be insensitive to most peptide sequences (Spohn et al., Vaccine, 22(19):2494-9, 2004). The peptide may comprise a sequence set forth in Table 1, any sequence at least 80%, 85%, 90%, or 95% identical thereto, or any analog, derivative, fragment, homolog, variant or substitution thereof. The peptide may carry a net negative charge.

TABLE 1

| Sequence | Length | SEQ ID NO |
|---|---|---|
| SNNA | 4 | 1 |
| GSSHH | 5 | 2 |
| KQNVS | 5 | 3 |
| NNSGK | 5 | 4 |
| QPDRY | 5 | 5 |
| RPDRY | 5 | 6 |
| SEEEE | 5 | 7 |
| SKKKK | 5 | 8 |
| SNNNA | 5 | 9 |
| SPPPP | 5 | 10 |
| GQHHM | 5 | 11 |
| GQHHH | 5 | 12 |
| SSHHM | 5 | 13 |
| GSHHM | 5 | 14 |
| SQMHH | 5 | 15 |
| GETDK | 5 | 16 |
| GEESN | 5 | 17 |
| GEEDD | 5 | 18 |
| TENVKE | 6 | 19 |
| QGEESNDK | 8 | 20 |
| VQGEESNDK | 9 | 21 |
| FEPPPATTT | 9 | 22 |
| GDKYFKETE | 9 | 23 |
| GDPKHPKSF | 9 | 24 |
| GGQEKSAAG | 9 | 25 |
| GPCPGCPPC | 9 | 26 |
| PPCPGCPPC | 9 | 27 |
| DNEEKPTPEQD | 11 | 28 |
| GNGGAPAQPKG | 11 | 29 |
| FEPPPATTTKSK | 12 | 30 |
| GNNDESNISFKEK | 13 | 31 |
| GDPKHPKSFTGWVA | 14 | 32 |
| AQNPNKTNSNLDSSK | 15 | 33 |
| NKDNEAEPVTEGNAT | 15 | 34 |
| SKEGNGPDPDNAAKS | 15 | 35 |
| GDKTPSTKSAGKVENK | 16 | 36 |
| GETDKEGKIIRIFDNSF | 17 | 37 |
| SSTSENNGNGNGNGGTD | 17 | 38 |
| GNNDESNISFKEKSEEEE | 18 | 39 |
| GNNDESNISFKEKSKKKK | 18 | 40 |
| GNNDESNISFKEKSPPPP | 18 | 41 |
| SSNKSTTGSGETTTAAGT | 18 | 42 |
| CGNNDESNISFKEKSKKKK | 19 | 43 |
| GSPLSFESSVQLIVSDNSS | 19 | 44 |
| SNYAKKVVKQKNHVYTPVY | 19 | 45 |
| ADVIAKIVEIVKGLIDQFTQK | 21 | 46 |
| GAASSLTYESSVQLVVSDNSS | 21 | 47 |
| GGEPAAQAPAETPAAAAEAAS | 21 | 48 |
| GQTDNNSSQSQQPGSGTTNT | 21 | 49 |
| SGALAATSDDDVKKAATVAIVA | 22 | 50 |
| SIVSTIIEVVKTIVDIVKKFKK | 22 | 51 |
| SSGGGGVAADIGAGLADALTAP | 22 | 52 |

The first four to five amino acids of the peptide moiety of a lipopeptide may be selected from those listed for each position in Table 2. This table is based upon Spohn et al., Vaccine, 22(19):2494-9, 2004; and Reutter et al., J. Peptide Res., 65, 375-383, 2005.

TABLE 2

| 1 | 2 | 3 | 4 | 5 |
|---|---|---|---|---|
| D | D | A | D | D |
| E | E | D | E | E |
| F | G | E | H | H |
| G | K | G | N | K |
| K | P | H | R | M |
| Q | Q | M | S | N |
| R | R | R | T | R |
| S | S | S |   | S |
|   | T | T |   |   |

The lipopeptide may be an RR- or RS-stereoisomer, or mixture thereof, with respect to the stereochemistry of the N-terminal lipoamino acid. The lipopeptide may be water-soluble.

3. Treatment of Stress

An agent that induces NF-κB activity may be used to protect normal cells from conditions or treatments that cause cellular stress, thereby triggering apoptosis. Representative examples of conditions or treatments include cancer treatments, e.g., radiation therapy or chemotherapy; temperature shock; exposure to harmful doses of radiation, e.g., workers in nuclear power plants, the defense industry or radiopharmaceutical production, or soldiers; cell aging; wounding; poisoning; and infection.

The agent may be administered simultaneously or metronomically with other treatments. The term "simultaneous" or "simultaneously" as used herein, means that the agent and other treatment be administered within 48 hours, preferably 24 hours, more preferably 12 hours, yet more preferably 6 hours, and most preferably 3 hours or less, of each other. The term "metronomically" as used herein means the administration of the agent at times different from the other treatment and at a certain frequency relative to repeat administration.

The agent may be administered at any point prior to exposure to the stress including, but not limited to, about 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, or 1 hr prior to exposure. The agent may be administered at any point after exposure to the stress including, but not limited to, about 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, or 48 hr after exposure.

a. Constitutively Active NF-κB Cancer

The condition may be a constitutively active NF-κB cancer. The agent that induces NF-κB activity may be administered in combination with a cancer treatment, such as chemotherapy or radiation therapy.

The cancer treatment may comprise administration of a cytotoxic agent or cytostatic agent, or combination thereof. Cytotoxic agents prevent cancer cells from multiplying by: (1) interfering with the cell's ability to replicate DNA and (2) inducing cell death and/or apoptosis in the cancer cells. Cytostatic agents act via modulating, interfering or inhibiting the processes of cellular signal transduction that regulate cell proliferation.

Classes of compounds that may be used as cytotoxic agents include the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxyco-formycin, mitomycin-c, 1-asparaginase, interferons (preferably IFN-α), etoposide, and teniposide.

Other proliferative cytotoxic agents are navelbene, CPT-11, anastrazole, letrazole, capecitabine, reloxafine, cyclophosphamide, ifosamide, and droloxafine.

Microtubule affecting agents interfere with cellular mitosis and are well known in the art for their cytotoxic activity. Microtubule affecting agents that may be used include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, MAP4, and the like. Examples of such agents are also described in Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; and Panda (1996) J. Biol. Chem. 271:29807-29812.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Cytostatic agents that may be used include, but are not limited to, hormones and steroids (including synthetic analogs): 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminoglutethimide, estramustine, medroxyprogesteroneacetate, leuprolide, flutamide, toremifene, and zoladex.

Other cytostatic agents are antiangiogenics, such as matrix metalloproteinase inhibitors, and other VEGF inhibitors, such as anti-VEGF antibodies and small molecules such as ZD6474 and SU6668 are also included. Anti-Her2 antibodies from Genentech may also be utilized. A suitable EGFR inhibitor is EKB-569 (an irreversible inhibitor). Also included are Imclone antibody C225 immunospecific for the EGFR, and src inhibitors.

Also suitable for use as a cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

The cancer treatment may comprise radiation therapy. The radiation therapy may be external beam radiation, internal radiation therapy, or conformal radiation therapy, in which a computer is used to shape the beam of radiation to match the shape of the tumor. The radiation used in radiation therapy may come from a variety of sources, including an x-ray, electron beam, or gamma rays. The doses and timing of administration of the radiation during radiation therapy can and will vary depending on the location and extent of the cancer. The agent that induces NF-κB activity may be administered with a radioprotective agent (see section 3d) in combination with the radiation therapy, as described above.

Cancers that may be treated include, but are not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, larynx, pancreas (including exocrine pancreatic carcinoma), mouth, pharynx, esophagus, stomach, small intestine, colon, rectum, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; and other tumors including melanoma, xenoderma pigmentosum, keratoactanthoma, seminoma, thyroid follicular cancer, and teratocarcinoma.

b. Treatment of Side Effects from Cancer Treatment

The condition may also be damage to normal tissue attributable to the treatment of a constitutively active NF-κB cancer. The agent that induces NF-κB activity may be administered in combination with a cancer treatment as described above.

c. Modulation of Cell Aging

The condition may also be cell aging.

d. Radiation

The condition may also be exposure to radiation. Exposure to ionizing radiation (IR) may be short- or long-term, it may be applied as a single dose or multiple doses, to the whole body or locally. Thus, nuclear accidents or military attacks may involve exposure to a single high dose of whole body irradiation (sometimes followed by a long-term poisoning with radioactive isotopes). Likewise, a single dose of radiation is generally used for the pretreatment of bone marrow transplant patients when it is necessary to prepare the host's hematopoietic organs for the donor's bone marrow by "cleaning" them from the host blood precursors.

At the molecular and cellular level, radiation particles may lead to breakage in the DNA and cross-linking between DNA, proteins, cell membranes and other macromolecular structures. Ionizing radiation may also induce secondary damage to the cellular components by giving rise to free radicals and reactive oxygen species (ROS). Multiple repair systems counteract this damage, such as several DNA repair pathways that restore the integrity and fidelity of the DNA, and antioxidant chemicals and enzymes that scavenge the free radicals and ROS and reduce the oxidized proteins and lipids. Cellular checkpoint systems are present to detect the DNA defects and delay cell cycle progression until the damage is repaired or a decision to commit the cell to growth arrest or programmed cell death (apoptosis) is reached.

At the organism level, the immediate effects of low and moderate levels of radiation are largely caused by cell death, which leads to radiation-induced inflammation. At higher radiation levels, the so-called hematopoietic and gastrointestinal syndromes lead to short-term radiation-induced death. The hematopoietic syndrome is characterized by the loss of hematopoietic cells and their progenitors, thereby making it impossible to regenerate blood and the lymphoid system. Death usually occurs as a consequence of infection (due to immunosuppression), hemorrhage and/or anemia. The gastrointestinal syndrome is characterized by massive cell death in the intestinal epithelium, predominantly in the small intestine, followed by the disintegration of the intestinal wall and death from bacteriemia and sepsis. The hematopoietic syndrome manifests itself at lower doses of radiation and leads to a more delayed death than the gastrointestinal syndrome. Very high doses of radiation can cause nearly instant death by eliciting neuronal degeneration.

Organisms that survive a period of acute toxicity of radiation may suffer long-term consequences that include radiation-induced carcinogenesis and fibrosis that develop in exposed organs (e.g., kidney, liver or lungs) months and even years after irradiation.

Inducers of NF-κB possess strong pro-survival activity at the cellular level and may be used to treat the effects of natural radiation events, exposure to low doses of radiation, radiation administered as part of cancer therapy, or nuclear accidents. Moreover, since inducers of NF-κB acts through mechanisms different from all presently known radioprotectants, they may be used in combination with other radioprotectants, thereby, dramatically increasing the scale of protection from ionizing radiation.

Historically, radioprotectants have generally been antioxidants and free radical scavengers—both synthetic and natural. More recently, cytokines and growth factors have been added to the list of radioprotectants; the mechanism of their radioprotection is considered to be due to their facilitating effect on the regeneration of sensitive tissues. There is no clear functional distinction between the two groups of radioprotectants, however, since some cytokines induce the expression of the cellular antioxidant proteins, such as manganese superoxide dismutase (MnSOD) and metallothionein, their use may be advantageous.

The radioprotectants may be any agent that treats the effects of radiation exposure including, but not limited to, antioxidants, free radical scavengers, cytokines, flagellin and latent TGFβ. Antioxidants and free radical scavengers that may be used include, but are not limited to, thiols, such as cysteine, cysteamine, glutathione and bilirubin; amifostine (WR-2721); vitamin A; vitamin C; vitamin E; and flavonoids such as Indian holy basil (Ocimum sanctum), orientin and vicenin Cytokines and growth factors confer radioprotection by replenishing and/or protecting the radiosensitive stem cell populations. Cytokines that may be used include stem cell factor (SCF, c-kit ligand), Flt-3 ligand, interleukin-1 fragment IL-1b-rd, and keratinocyte growth factor (KGF). Several other factors, while not cytokines by nature, stimulate the proliferation of the immunocytes, and thus, may be used. These include, 5-AED (5-androstenediol), which is a steroid that stimulates the expression of cytokines, and synthetic compounds, such as ammonium tri-chloro(dioxoethylene-O, O'—) tellurate (AS-101). Latent TGFβ, flagellin and flagellin derivatives are strong inducers of NF-κB activity as shown in International Patent Application Nos. PCT/US2004/040656 and PCT/US2004/040753, and U.S. Patent Application No. 60/693,826, the contents of which are incorporated herein by reference.

4. Composition

Provided herein also are compositions comprising a therapeutically effective amount of an inducer of NF-κB. The composition may be a pharmaceutical composition, which may be produced using methods well known in the art. As described above, the composition comprising an inducer of NF-κB may be administered to a mammal for the treatment of conditions associated with apoptosis including, but not limited to, exposure to radiation, side effect from cancer treatments, stress and cell aging. The composition may also comprise additional agents including, but not limited to, a radioprotectant or a chemotherapeutic drug.

a. Administration

Compositions provided herein may be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intraarticular. For veterinary use, the composition may be administered as a suitably acceptable formulation in accordance with normal veterinary practice. The veterinarian can readily determine the dosing regimen and route of administration that is most appropriate for a particular animal.

b. Formulation

Compositions provided herein may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions provided herein may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Compositions provided herein may also be formulated as suppositories, which may contain suppository bases including, but not limited to, cocoa butter or glycerides. Compositions provided herein may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions provided herein may also be formulated as transdermal formulations comprising aqueous or nonaqueous vehicles including, but not limited to, creams, ointments, lotions, pastes, medicated plaster, patch, or membrane.

Compositions provided herein may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions provided herein may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

c. Dosage

A therapeutically effective amount of the agent required for use in therapy varies with the nature of the condition being treated, the length of time that induction of NF-κB activity is desired, and the age and the condition of the patient, and is ultimately determined by the attendant physician. In general, however, doses employed for adult human treatment typically are in the range of 0.001 mg/kg to about 200 mg/kg per day. The dose may be about 1 μg/kg to about 100 μg/kg per day. The desired dose may be conveniently administered in a single dose, or as multiple doses administered at appropriate intervals, for example as two, three, four or more sub-doses per day. Multiple doses often are desired, or required, because NF-κB activity in normal cells may be decreased once the agent is no longer administered.

The dosage of an inducer of NF-κB may be at any dosage including, but not limited to, about 1 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg or 1 mg/kg.

5. Screening Methods

The method provided herein also relates to methods of identifying agents that induce NF-κB activity. An agent that induces NF-κB activity may be identified by a method comprising adding a suspected inducer of NF-κB activity to an NF-κB activated expression system, comparing the level of NF-κB activated expression to a control, whereby an inducer of NF-κB activity is identified by the ability to increase the level of NF-κB activated expression system.

Candidate agents may be present within a library (i.e., a collection of compounds). Such agents may, for example, be encoded by DNA molecules within an expression library. Candidate agents may be present in conditioned media or in cell extracts. Other such agents include compounds known in the art as "small molecules," which have molecular weights less than $10^5$ daltons, preferably less than $10^4$ daltons, and still more preferably less than $10^3$ daltons. Such candidate agents may be provided as members of a combinatorial library, which includes synthetic agents (e.g., peptides) prepared according to multiple predetermined chemical reactions. Those having ordinary skill in the art will appreciate that a diverse assortment of such libraries may be prepared according to established procedures, and members of a library of candidate agents can be simultaneously or sequentially screened as described herein.

The screening methods may be performed in a variety of formats, including in vitro, cell-based and in vivo assays. Any cells may be used with cell-based assays. Preferably, cells that may be used include mammalian cells, more preferably human and non-human primate cells. Cell-base screening may be performed using genetically modified tumor cells expressing surrogate markers for activation of NF-κB. Such markers include, but are not limited to, bacterial β-galactosidase, luciferase and enhanced green fluorescent protein (EGFP). The amount of expression of the surrogate marker may be measured using techniques standard in the art including, but not limited to, colorimetery, luminometery and fluorimetery.

The conditions under which a suspected modulator is added to a cell, such as by mixing, are conditions in which the cell can undergo apoptosis or signaling if essentially no other regulatory compounds are present that would interfere with apoptosis or signaling. Effective conditions include, but are not limited to, appropriate medium, temperature, pH and oxygen conditions that permit cell growth. An appropriate medium is typically a solid or liquid medium comprising growth factors and assimilable carbon, nitrogen and phosphate sources, as well as appropriate salts, minerals, metals and other nutrients, such as vitamins, and includes an effective medium in which the cell can be cultured such that the cell can exhibit apoptosis or signaling. For example, for a mammalian cell, the media may comprise Dulbecco's modified Eagle's medium containing 10% fetal calf serum.

Cells may be cultured in a variety of containers including, but not limited to tissue culture flasks, test tubes, microtiter dishes, and petri plates. Culturing is carried out at a temperature, pH and carbon dioxide content appropriate for the cell. Such culturing conditions are also within the skill in the art.

Methods for adding a suspected modulator to the cell include electroporation, microinjection, cellular expression (i.e., using an expression system including naked nucleic acid molecules, recombinant virus, retrovirus expression vectors and adenovirus expression), use of ion pairing agents and use of detergents for cell permeabilization.

This invention has multiple aspects, illustrated by the following non-limiting examples.

Example 1 p53 Deficiency Accelerates Development of the GI Syndrome in Mice

The primary cause of death from ionizing radiation (IR) of mammals depends on the radiation dose. At doses of up to 9-10 Gy, mice die 12-20 days later, primarily from lethal bone marrow depletion, i.e., the hematopoietic (HP) syndrome. At this dose, irradiated mice can be rescued from lethality by bone marrow transplantation. Animals that received >13-15 Gy die between 7-12 days after treatment (before hematopoietic syndrome could kill them) from complications of damage to the small intestine, i.e., the gastrointestinal (GI) syndrome.

It is well known that cell proliferation of the epithelial cells of the small intestine is limited to the crypts where stem cells and early proliferating progenitors are located. After a couple of cell divisions, already differentiated descendants of crypt stem cells move up the villi to be shed at the villar tip. In the small intestine of the mouse, the entire "trip" of the cell (i.e., from the proliferative compartment to the tip of the villus) normally takes between 3 and 5 days. Although reaction of the small intestine to gamma radiation has been well examined at a pathomorphological level, the exact cause of GI lethality, including the primary event, still remains unclear. Death may occur as a direct consequence of the damage to the epithelial crypt cells, followed by denudation of the villi leading to fluid and electrolyte imbalance, bacteremia, and endotoxemia. In addition to inflammation and stromal responses, endothelial dysfunctions appear to be important factors contributing to lethality.

In both the HP and GI syndromes, lethal tissue damage results from massive p53 dependent apoptosis. Furthermore, it has been shown that p53 dependent hair loss (alopecia) occurs as a result of experimental chemotherapy or radiation. Thus, it appears that p53 could play a role in sensitizing cells to genotoxic stress.

To examine the role of p53 in radiation-induced death, mice were treated with the small molecule inhibitor of p53, pifithrin-alpha (PFTα) (Komarov et al., Science 285:1733-7, 1999) immediately prior to gamma irradiation. C57B1/6J mice (6-8 weeks old males were used here and below, if not indicated otherwise) were injected intraperitoneally with 10 mg/kg of PFTa and then irradiated using a Shepherd 4000 Ci $^{137}$Cesium source at a dose rate of 4 Gy per minute. PFTα protected mice from a single 9 Gy dose of gamma radiation or a fractioned cumulative radiation dose of 12.5 Gy (5×2.5 Gy). In contrast, PFTa had no effect on the survival of mice treated with single high doses, i.e., 12.5 or 25 Gy, of IR (FIG. 1a).

Figure 1C:
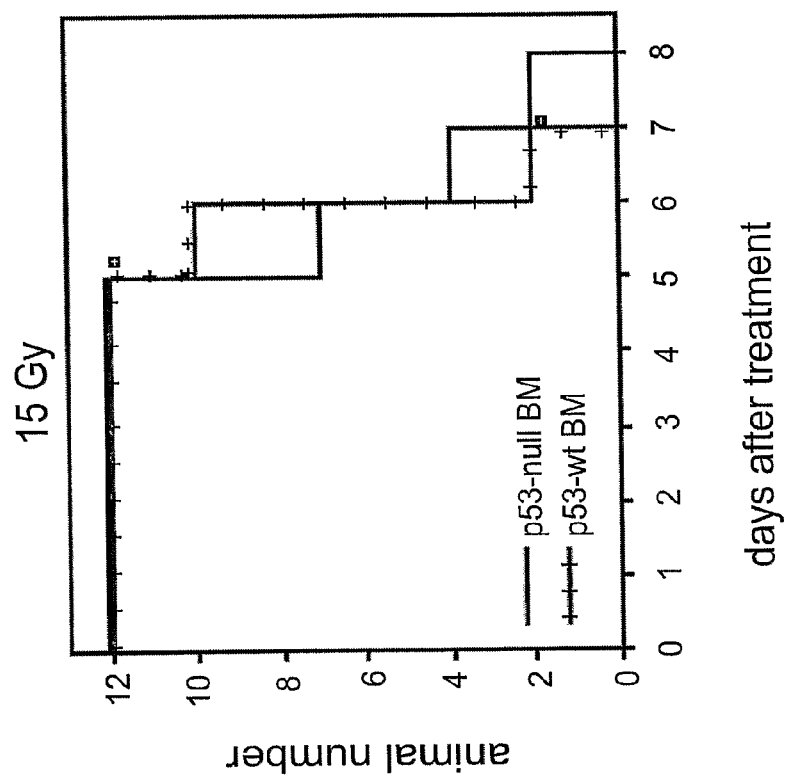
FIG. 1c presents a graph illustrating the percent survival of mice exposed to 15 Gy of total body gamma radiation following reconstitution with bone marrow (BM) from wild type or p53-null mice.
Figure 1D:
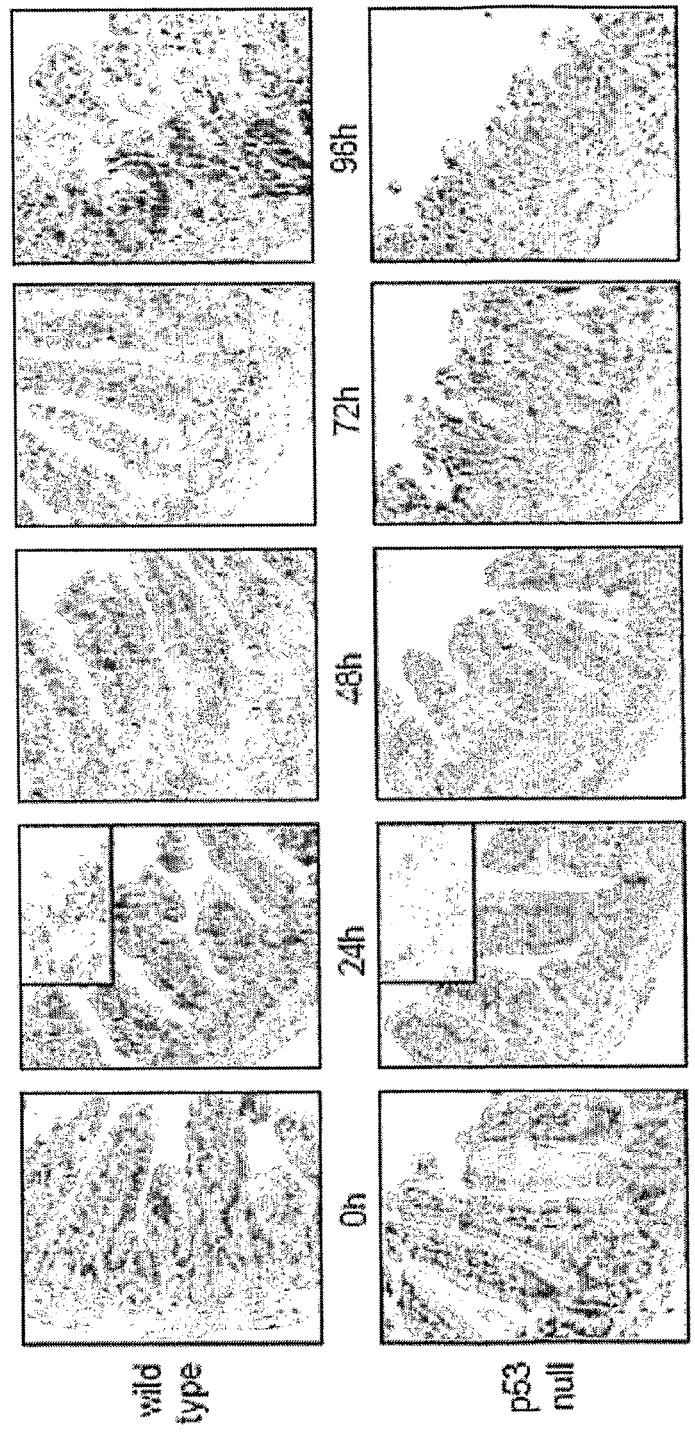
FIG. 1d presents haematoxylin-eosin stained paraffin intestinal sections from wild type and p53-null mice at the indicated time points after 15 Gy of gamma radiation. Insets at 24 h show TUNEL staining of crypt regions.

To further examine the role of p53 in the GI syndrome, wild type and p53-deficient mice were exposed to low (10 Gy) and high (15 Gy) doses of gamma radiation. As shown in FIG. 1b, p53-deficient mice were resistant to low doses of radiation that kill through the HP syndrome, but much more sensitive to higher doses of radiation that kill through the GI syndrome. Haematoxylin-eosin stained paraffin sections of the small intestinal from wild type and p53-null mice at 0, 24, 48, 72, and 96 hr after a 15 Gy dose of gamma radiation are shown in FIG. 1d. The p53-deficient mice exhibited accelerated epithelial cell damage. TUNEL staining in the crypts (at 24 hr) revealed that apoptosis was evident in wild type but not in p53-deficient epithelium. To examine this further, wild-type mice were exposed to 11 Gy of total body irradiation and then, 12 hr later, injected with $1.5 \times 10^7$ bone marrow cells from wild type or p53-null syngeneic C57B1/6J mice. (This dose of radiation caused 100% lethality in nonreconstituted control mice). Two months later, after complete recovery of hematopoiesis, the two groups of animals were treated with 15 Gy of total body gamma radiation. As shown in FIG. 1c, there was no difference in death rates between the two groups mice that differed in the p53 status of their bone marrow (both had wild-type intestinal cells).

Figure 2A:
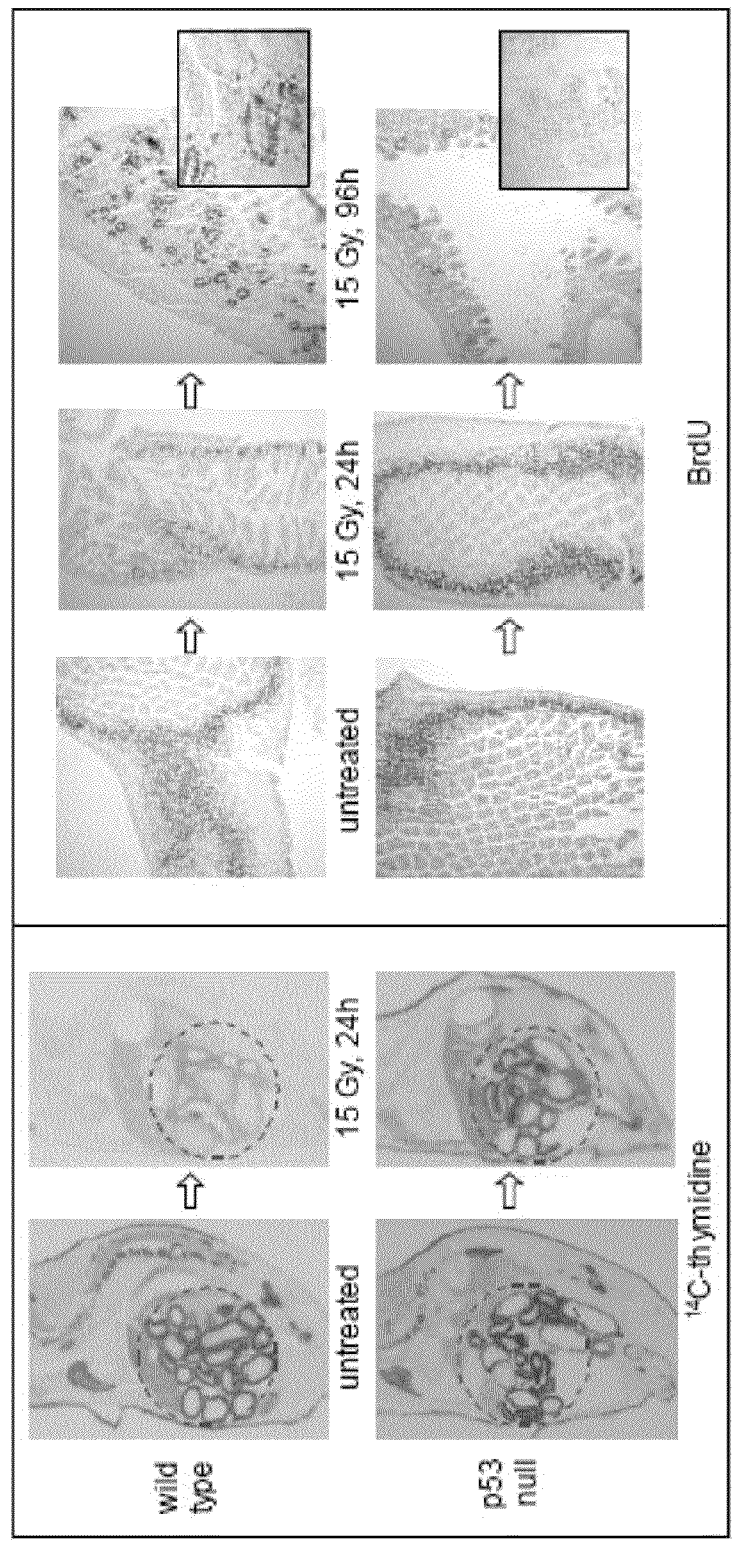
FIG. 2a (left) shows autoradiographs of whole-body sections of wild type and p53-null mice injected with 14C-thymidine that were treated with 15 Gy of gamma radiation or not treated. Arrows point to the intestines.

The dynamics of cell proliferation and cell survival were further examined in the small intestines of wild type and p53-null mice. Four-week old wild type and p53-null mice were injected intraperitoneally with $^{14}$C-thymidine (10 μCi per animal) and then half of each group was exposed to 15 Gy of gamma radiation. Autoradiographs of whole-body sections revealed that after 24 hrs, the cells in the intestinal crypts of p53-deficient mice continued to proliferate, whereas those in the wild type mice were quiescent (FIG. 2a, left). Four-week old wild type and p53-null mice were treated with 15 Gy of gamma radiation, and 2 hr before being sacrificed they were injected with BrdU (50 mg/kg) and the intestines were immunostained. At 24 hr after irradiation, there were many proliferating cells in the p53-null mice, but few in the wild type mice. In contrast, at 96 hr, there were few proliferating cells in the p53-null mice, whereas the wild type mice displayed more labeled cells.

Figure 2B:
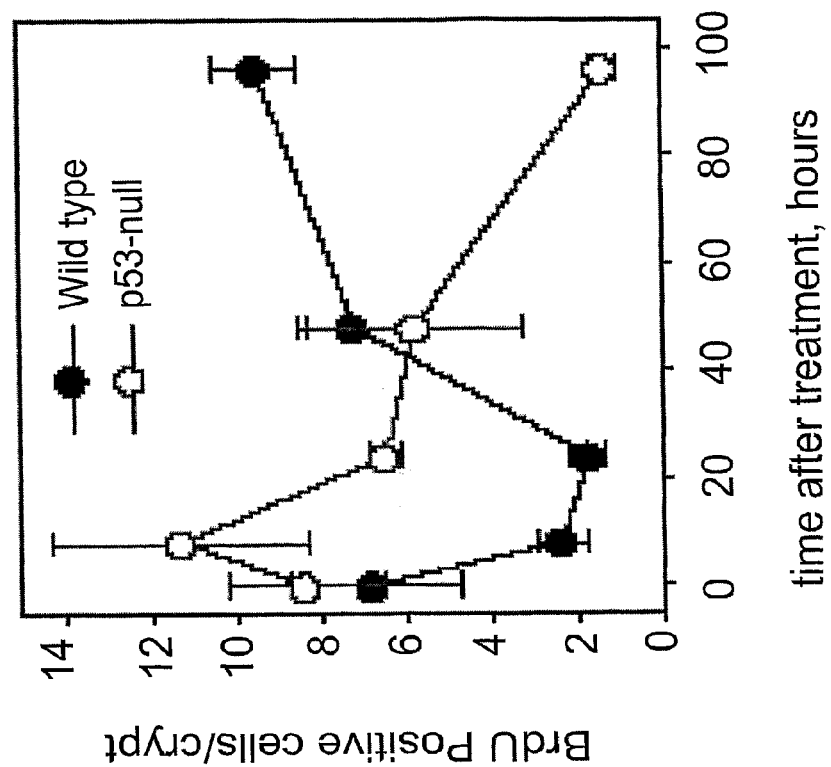
FIG. 2b presents a graph of the number of BrdU positive cells/crypt in the small intestine of wild type and p53-null mice at different time points after 15 Gy of gamma radiation.
Figure 2C:
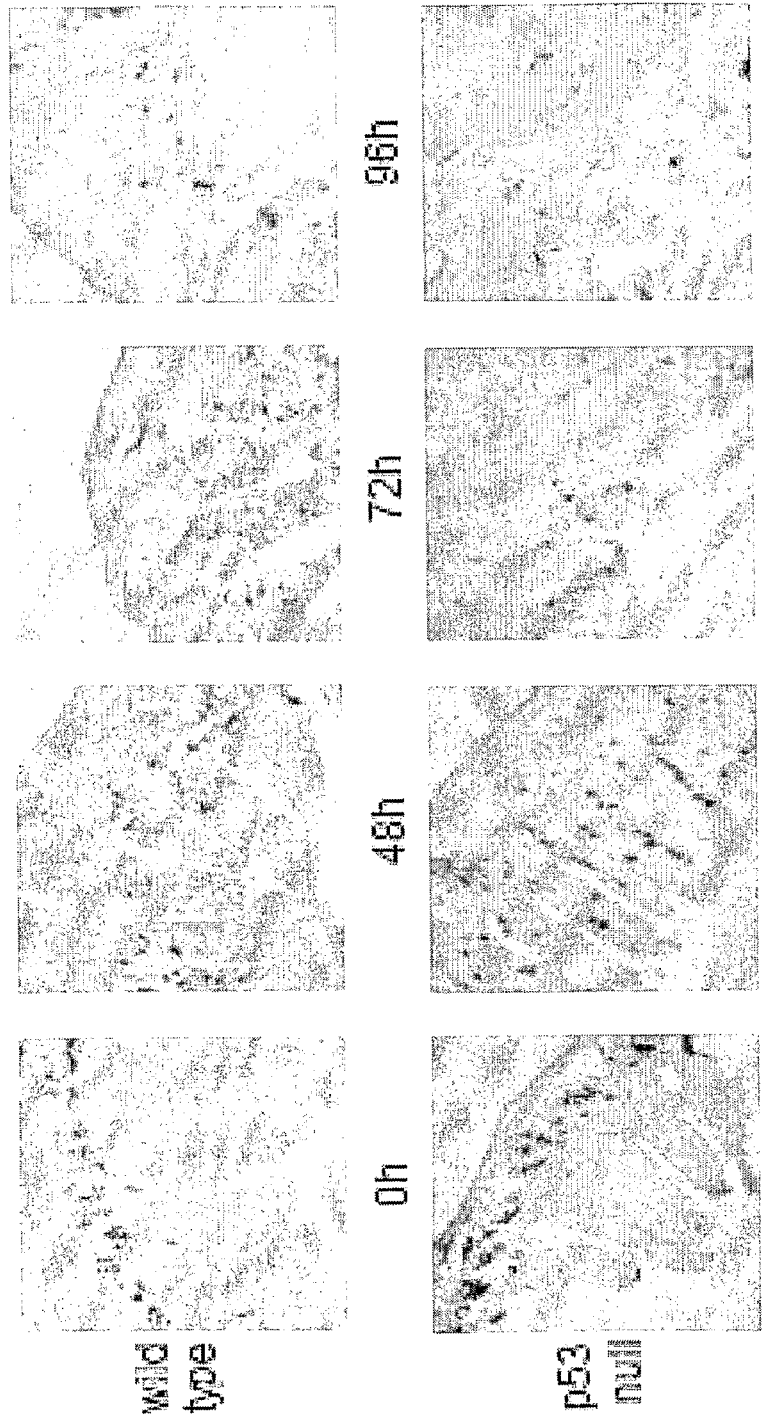
FIG. 2c presents photomicrographs of BrdU-labeled cells in the small intestine of wild type and p53-null mice at different time points after 15 Gy of gamma radiation. BrdU was injected 30 min before irradiation and the mice were sacrificed at the indicated time points.

To characterize this further, the number of BrdU positive cells were counted in the small intestines of wild-type and p53-null mice at different time points after 15 Gy of gamma radiation. Three animals were analyzed for each time point, five ilial cross sections were prepared from each animal and analyzed microscopically to estimate the number of crypts and villi. Numbers of BrdU-positive cells in the crypts were counted in five random fields under 200× magnification (100-300 crypts) and the average number of BrdU-positive cells was plotted (FIG. 2b). The number of BrdU-positive cells in the p53-null mice peaked at 10 hr and then declined, whereas the number of BrdU-positive cells in wild type mice declined during the first 20 hrs and then increased. The location of BrdU-labeled cells was traced in the small intestines of wild type and p53-null mice at different time points after 15 Gy of gamma radiation. BrdU was injected 30 min before irradiation and mice were sacrificed at 0, 48, 72, and 96 hr. In p53-null mice, there was an accelerated migration of BrdU-labeled cells from the crypts to the villi (compare wild type and p53-null at 48 hr), followed by rapid elimination of the labeled cells in p53-null mice (FIG. 2c).

Thus, continuous cell proliferation in the crypts of irradiated p53-deficient epithelium correlates with the accelerated death of damaged cells of the crypt and rapid destruction of the villi. In wild type mice, however, p53 prolongs survival by inducing growth arrest in the crypts of the small intestine, thereby preserving integrity of the intestine. Thus, the proapoptotic function of p53 promotes the hematopoietic syndrome, while its growth arrest function delays development of the gastrointestinal syndrome. Thus, pharmacological suppression of p53 would be useless (if not detrimental) against the GI syndrome. Therefore, it is necessary to develop alternative approaches to radioprotection of epithelium of small intestine that will rely on another mechanism, such as, for example, activation of NF-κB and subsequent inhibition of cell death.

Example 2

Lipopeptides Delay Mouse Death Caused by Total Body Gamma-Irradiation

Lipopeptides are potent activators of NF-κB and, as such, may act as inhibitors of apoptotic death. To determine whether lipopeptides function as radioprotectants, various lipopeptides were initially tested to determine the maximal tolerable dose (MTD). Various lipopeptides were then tested to measure their protective effect in NIH Swiss mice to lethal hematopoietic or nd gastrointestinal syndromes after exposure to 10 Gy or 13-15 Gy of total body gamma radiation, respectively. Lipopeptides (0.3-10 μg/mouse) were administered subcutaneously 30 minutes prior to irradiation. Lipopeptides tested that provided radioprotection are set forth in Table 3.

TABLE 3

| Peptide Sequence | SEQ ID NO | Peptide Length | N-acylation |
|---|---|---|---|
| SKKKK | 8 | 5 | R-Pam2 |
| SKKKK | 8 | 5 | R-Parn3 |
| FEPPPATTT | 22 | 9 | Pam2 |
| GNNDESNISFKEK | 31 | 13 | Pam2 |
| GDPKHPKSF | 24 | 9 | Pam2 |
| GETDKEGKIIRIFDNSF | 37 | 17 | Pam2 |

Figure 3:
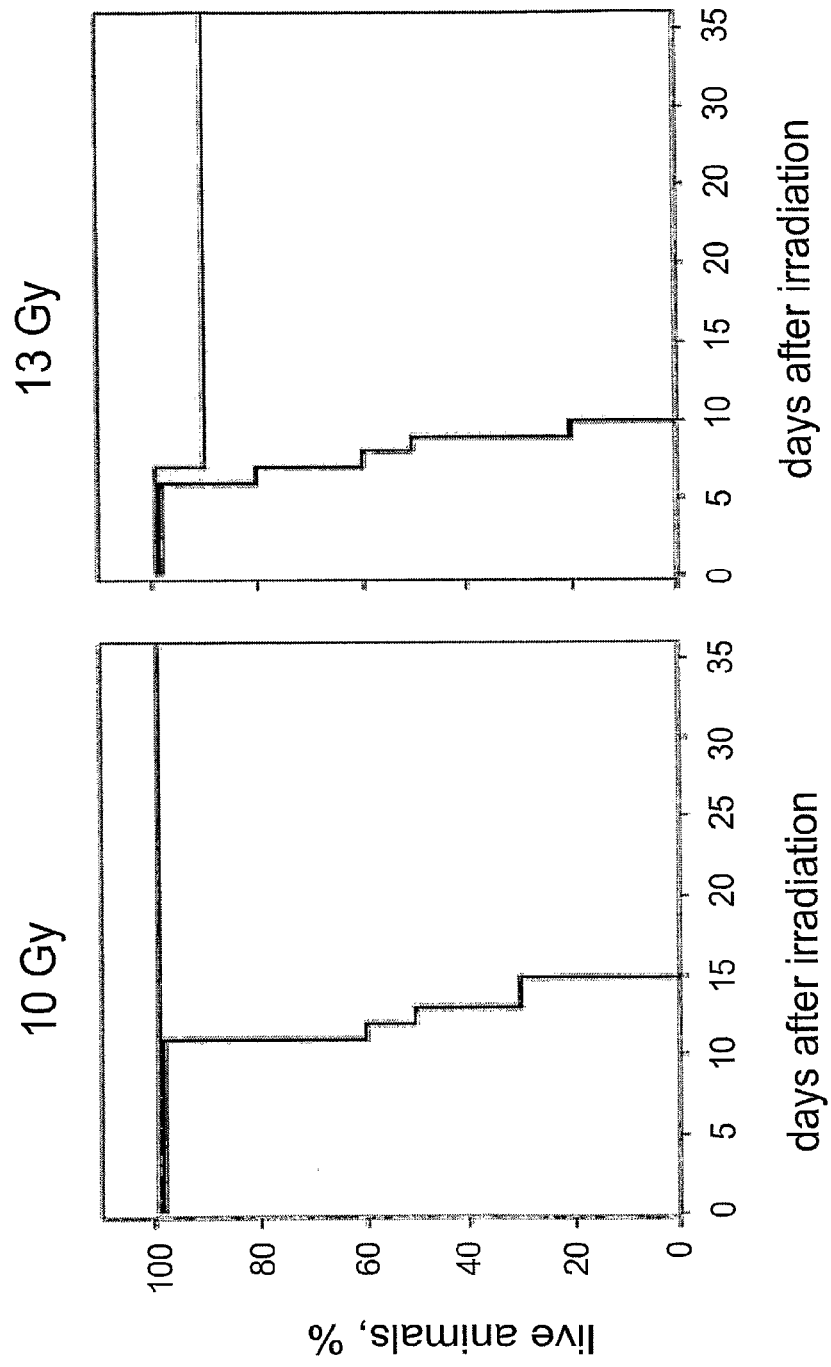
FIG. 3 illustrates the radioprotective effect of the compound, CBLB601. Shown are graphs of the percent of survival of mice exposed to 9, 12.5, 25, or 5×2.5 Gy of total body gamma radiation following pretreatment with CBLB601 or PBS.
Figure 4:
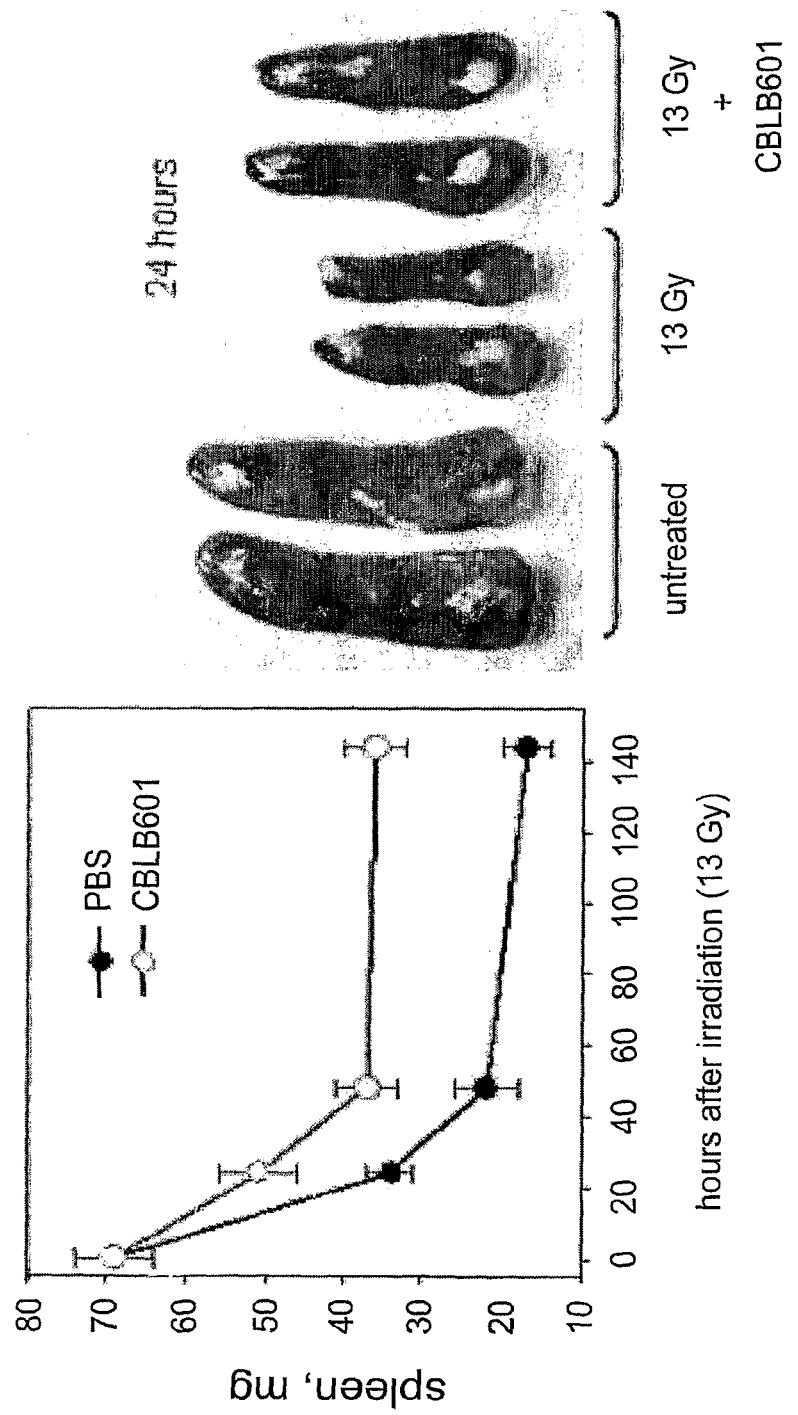
FIG. 4 illustrates alterations in spleen size after exposure to 13 Gy of total body gamma irradiation following pre treatment with CBLB601 or PBS. On the left is a graph of spleen weights of PBS and CBLB601-treated mice, and on the right are images of spleens from the control or treated mice.

The results of a representative experiment using R-PAM$_2$C-SKKKK (SEQ ID NO: 8) (hereafter, this compound is called, CBLB601) at <0.1 MTD are shown in FIG. 3. As expected, control mice irradiated with 10 Gy died between 11 and 15 days post-treatment, while all animals that received CBLB601 lived beyond 35 days post-treatment. Similarly, control mice irradiated with 13 Gy died between 6 and 10 days post-treatment, while all but one animal that received CBLB601 lived beyond 35 days post-treatment. The radioprotective ability of CBLB601 was further analyzed by measuring the effect of radiation on spleen size. As shown in FIG. 4, mice treated with CBLB601 showed significantly less reduction in the size of the spleen. CBLB601 also protected the thymus from radiation (data not shown). The ability of CBLB601 to effectively protect splenocytes, support fast recovery of the thymus, and protect the GI tract from radiation damage indicates that lipopeptides may be used as radioprotectants.

Example 3

Radioprotective Efficacy of a Single Dose of CBLB601 Against Total Body Gamma-Irradiation CBLB601, a R-Pam$_2$-lipopeptide with the peptide moiety consisting of C-SKKKK (SEQ ID NO: 8), was selected for more detailed characterization as a radioprotector based upon its ability to activate NF-κB and preliminary in vivo data on radioprotection in NIH-SWISS mice (see Example 2). The objectives of this study were to determine the optimal dose, route of administration, and time of administration of CBLB601 to serve as a protector. ICR female mice of 10-15 weeks of age were used, with 10-15 animals per group or condition.

The dose of NOAEL (No Obvious Adverse Effects Level) was determined by injecting intraperitoneally (i.p) ICR mice with the increasing doses of CBLB601 (0.3, 1, 3, 10, 30, 60, 100 μg/mouse). Control mice were injected with PBS. The mice were observed for two weeks. During the first week they were weighed daily. There were no differences in weight between the CBLB601-treated and control mice. Mortality was observed 1-2 days post-treatment at the 100 μg of CBLB601/mouse, but not at any of the lower doses. However, at 60 μg dose, the mice showed signs of morbidity, such as slow motion and scruffy fur, around 3-4 days after treatment. At the 30 μg dose, there were no noticeable differences between the treated and control mice. Thus, NOAEL for CBLB601 was determined to be 30 μg/mouse.

Figure 5A:
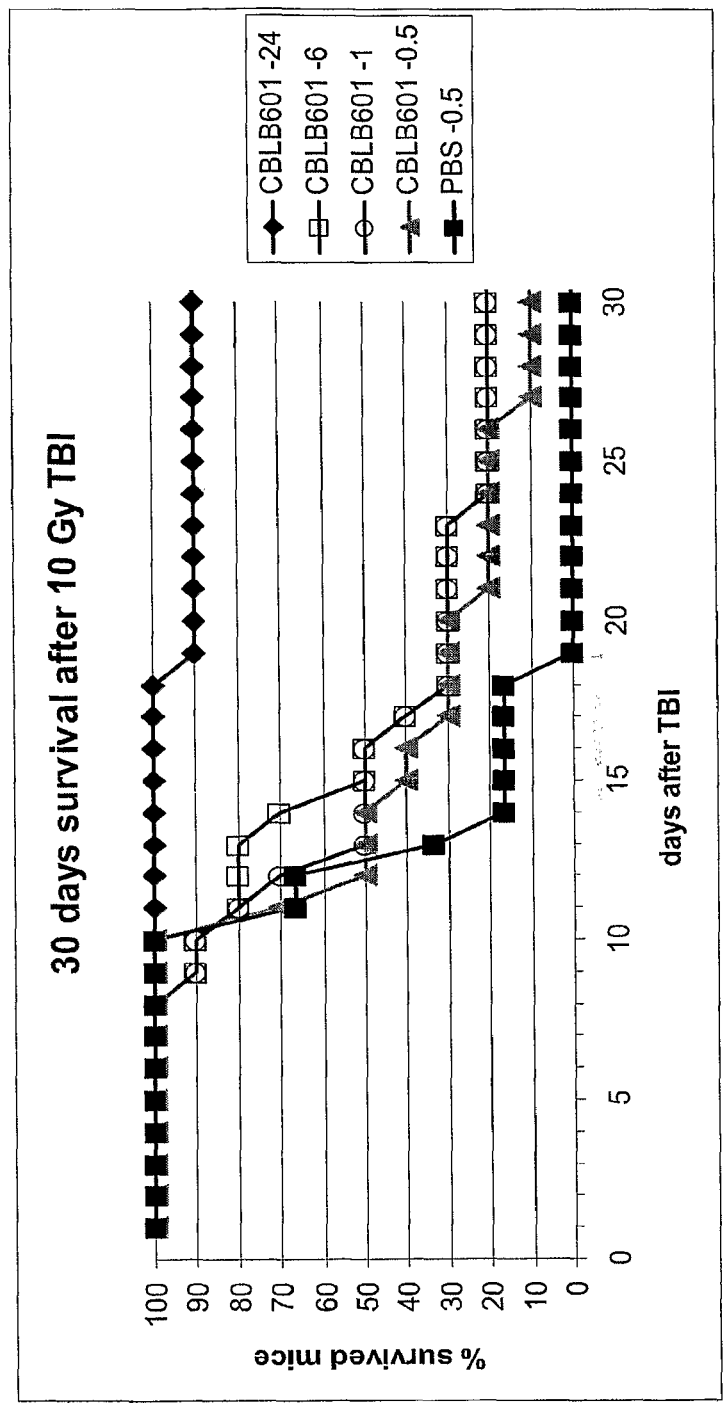
FIG. 5a shows a graph of the percent survival of mice exposed to 10 Gy of total body irradiation (TBI) following intraperitoneal administration of PBS or CBLB601 24, 6, 1 or 0.5 hr prior to irradiation.
Figure 5B:
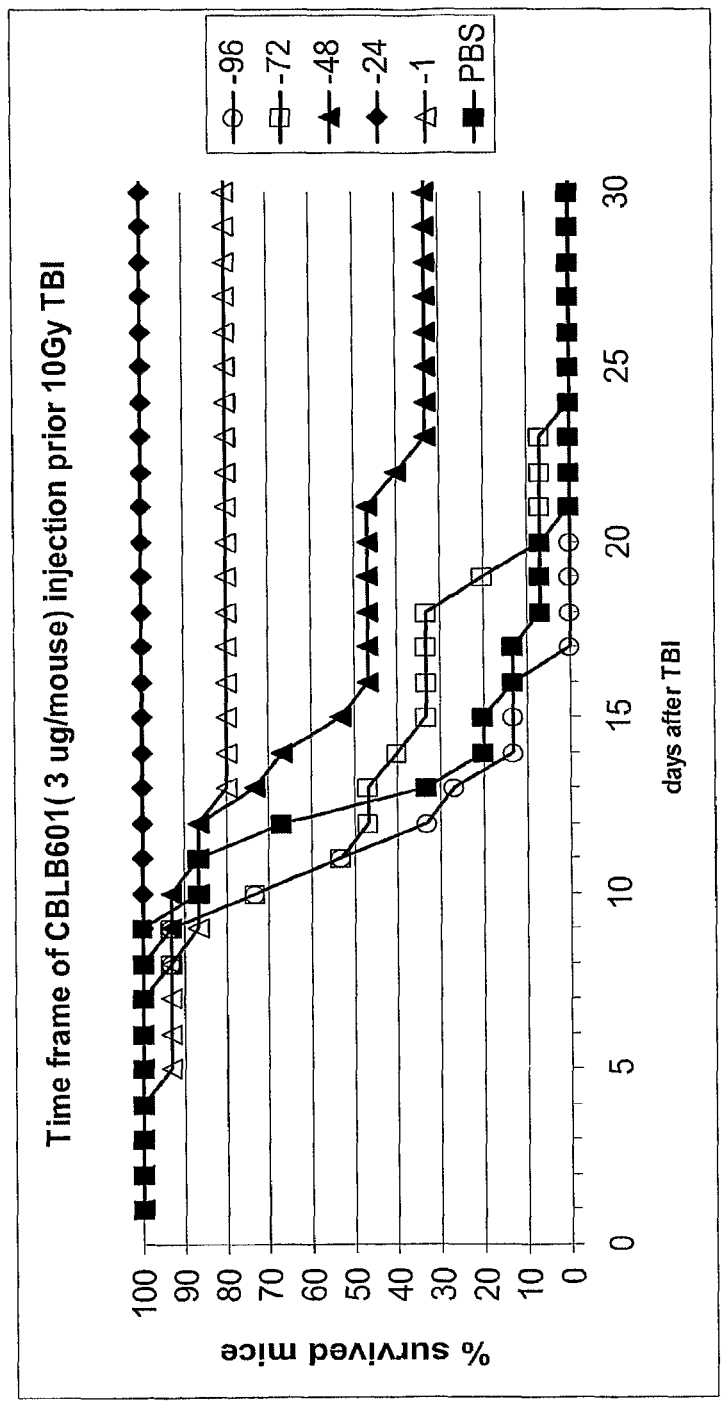
FIG. 5b shows a graph of the percent survival of mice exposed to 10 Gy of TBI following intraperitoneal administration of PBS or CBLB601 96, 72, 48, 24 or 1 hr prior to irradiation.

The optimal intraperitoneal administration schedule of CBLB601 was determined by injecting the compound at different times prior to irradiation. Previously, it was found that CBLB601 was protective against 10 Gy but not higher irradiation doses (see Example 2). Therefore, all of the optimization experiments were performed with 10 Gy of total body irradiation (TBI). A dose of 3 μg of BCLB601/mouse (1/10 NOAEL) was chosen as the starting dose. Thus, 3 μg of CBLB601 was injected i.p. into ICR mice at 0.5 h, 1 h, 6 h, and 24 h or 1 h, 24 h, 48 h, 72 h, 96 h prior to 10 Gy of TBI (as described in Example 1). Following irradiation, the mice were observed for 30 days and their survival was recorded. The results of these experiments are summarized in FIG. 5. Injection of CBLB601 24 hrs before irradiation clearly yielded the best radioprotection (90-100% 30-day survival). When the compound was administered 48 hrs before irradiation, the radioprotection was ~30%. Administration of CBLB601 at 1 hr prior to irradiation produced inconsistent results ranging from 80% protection in one experiment (FIG. 5B) to almost no protection (20%) in another experiment (FIG. 5A). No radioprotection was observed when the drug was administered at 0.5 h (10%), 6 h (20%), 72 h, and 96 h prior to TBI.

Figure 6A:
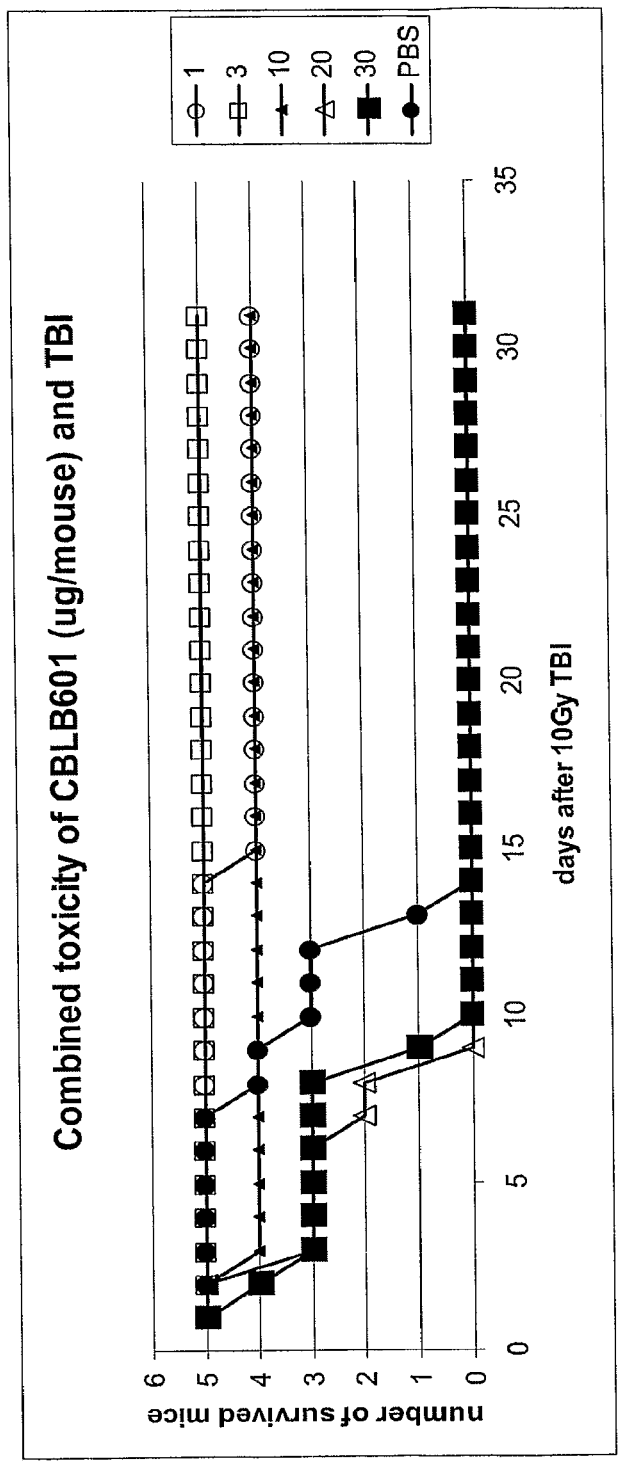
FIG. 6a shows a graph of the percent survival of mice exposed to 10 Gy of TBI following intraperitoneal administration of PBS or 1, 3, 10, 20, 30 μg of CBLB601/mouse 24 hr prior to irradiation.
Figure 6B:
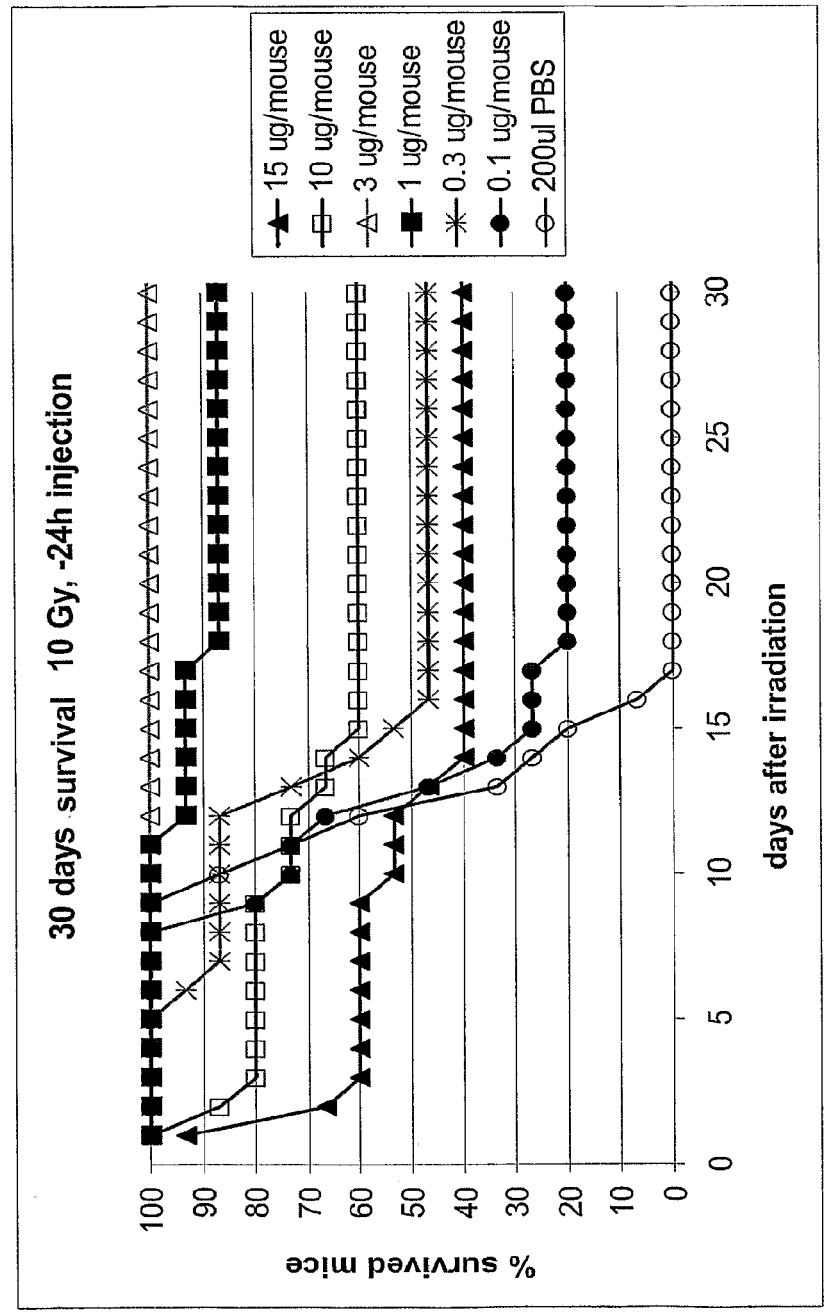
FIG. 6b shows a graph of the percent survival of mice exposed to 10 Gy of TBI following intraperitoneal administration of PBS or 0.1, 0.3, 1, 3, 10, or 15 μg of CBLB601/mouse 24 hr prior to irradiation.

To determine the optimal radioprotective dose of CBLB601, the timing of injection and level of irradiation were kept constant, while the dose of CBLB601 was varied. ICR mice were injected i.p. with 1, 3, 10, 20, or 30 μg of CBLB601/mouse or 0.1, 0.3, 1, 3, 10, or of CBLB601/mouse 24 hrs prior to irradiation (10 Gy of TBI), and their survival was monitored for 30 days. The best protective dose was 3 μg/mouse, which supported a survival of 100% (FIGS. 6 A and B). Almost similar efficacy was reached with the 1 and 10 μg/mouse doses, which rescued 90% of the mice (in one experiment). In contrast, higher doses of CBLB601 (20 and 30 μg/mouse) led to accelerated mortality when administered in combination with irradiation, as compared to PBS injected control mice. Some signs of this combined toxicity were detectable already at the 10 μg/mouse dose. Thus, the optimal protective dose of CBLB601 was determined to be 3 μg/mouse. Thus, while it appears that CBLB601 conferred radioprotection at doses 10-30-fold lower than the NOAEL, the margins of safety of CBLB601 were significantly reduced when CBLB601 was administered in combination with irradiation.

Figure 7A:
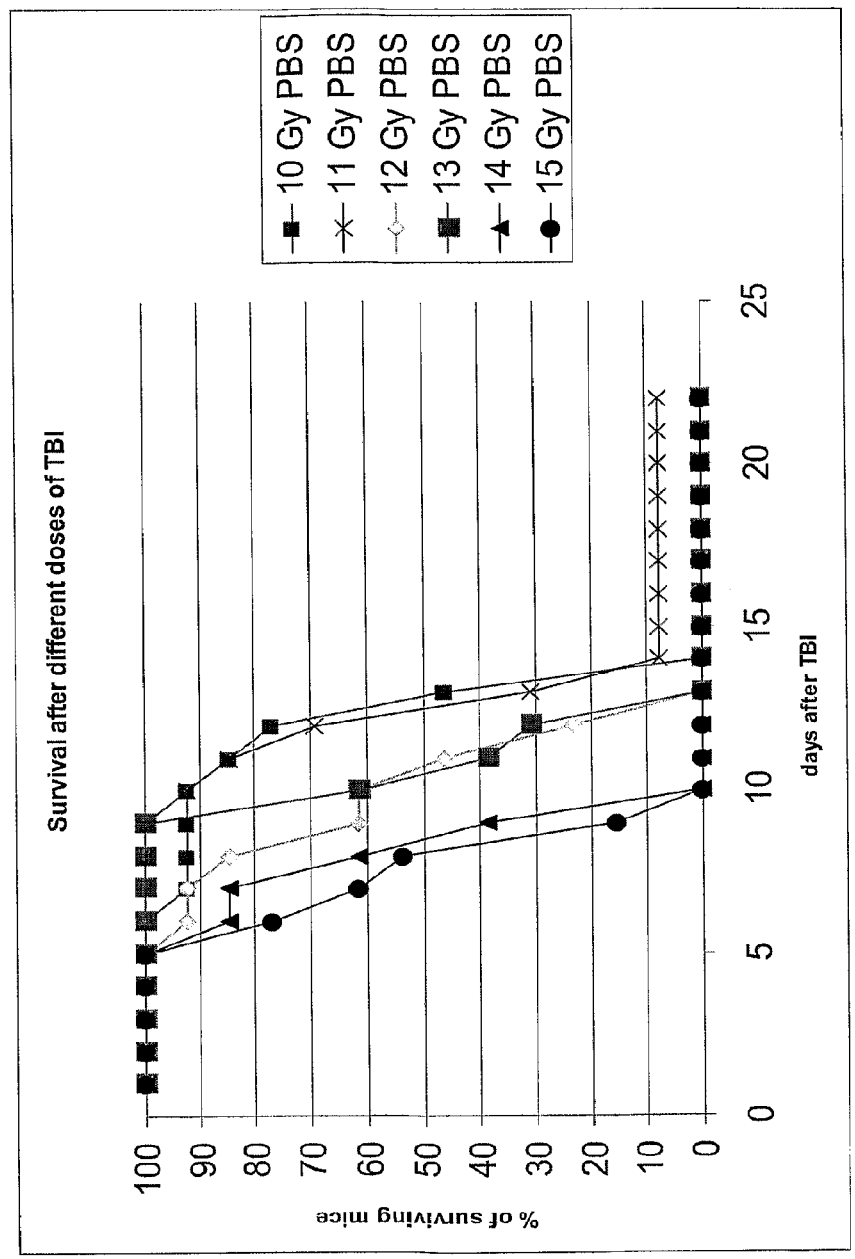
FIG. 7a shows a graph of the percent survival of mice exposed to 10, 11, 12, 13, 14, or 15 Gy of TBI following intraperitoneal administration of PBS 24 hr prior to irradiation.
Figure 7B:
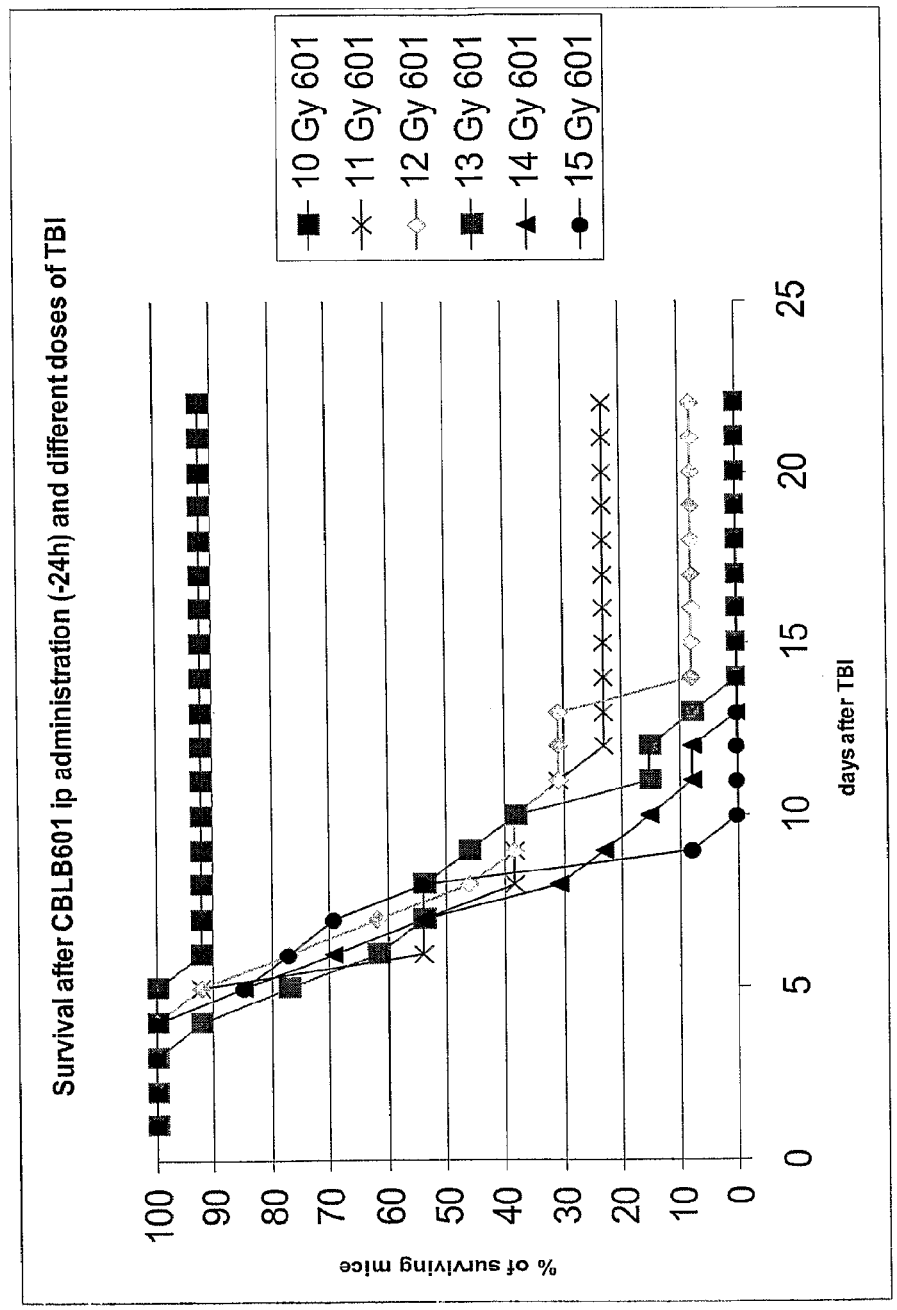
FIG. 7b shows a graph of the percent survival of mice exposed to 10, 11, 12, 13, 14, or 15 Gy of TBI following intraperitoneal administration of 3 μg of CBLB601/mouse 24 hr prior to irradiation.

To determine the level of radiation that was protected by CBLB601, radioprotectant-treated and control mice were exposed to increasing levels of TBI. Groups of ICR mice were injected i.p. with either 3 μg CBLB601/mouse or PBS, and then 24 h later they received 10, 11, 12, 13, 14, and 15 Gy doses of TBI. Survival was recorded over 30 days. FIG. 7A shows the radiation dose-dependent mortality of mice injected with PBS. All of the mice irradiated with 10-11 Gy of TBI died between days 12-14 post irradiation, which was typical for death due to hematopoietic failure. All of the mice that received 14-15 Gy of TBI died between days 7-9 post irradiation, which was typical for mortality due to radiation-induced intestinal damage. Mice that were irradiated with 12-13 Gy of TBI died at intermediate times, which was typical for a mixed etiology of radiation-induced mortality. FIG. 7B shows the radiation dose-dependent mortality of mice pretreated with CBLB601. Mice injected with 3 μg of CBLB601 24 hrs prior to irradiation were, as expected, fully protected from 10 Gy of TBI. Despite the obvious differences in survival between the control and treated mice, the protective effects of CBLB601 did not reach statistical significance under this setting. To reach a statistically significant 10% difference between control and CBLB601-treated mice, experimental groups of at least 50 mice must be used. Although CBLB601 rescued 100% of mice from 10 Gy of TBI, its protection at 11 Gy of TBI was only 20%. There was no protection from irradiation at levels higher than 11 Gy, indicating that CBLB601 was unable to rescue animals from the gastrointestinal component of radiotoxicity. Moreover, at irradiation doses of 11, 12 and 13 Gy, the CBLB601-treated mice died with an accelerated kinetics, i.e., similar to those that received 14-15 Gy doses, as compared to PBS-injected control mice. This may be indicative of a combined toxicity of the drug and the irradiation. Thus, it appears that at higher irradiation levels, CBLB601 did not confer protection and it was also more toxic.

Figure 8:
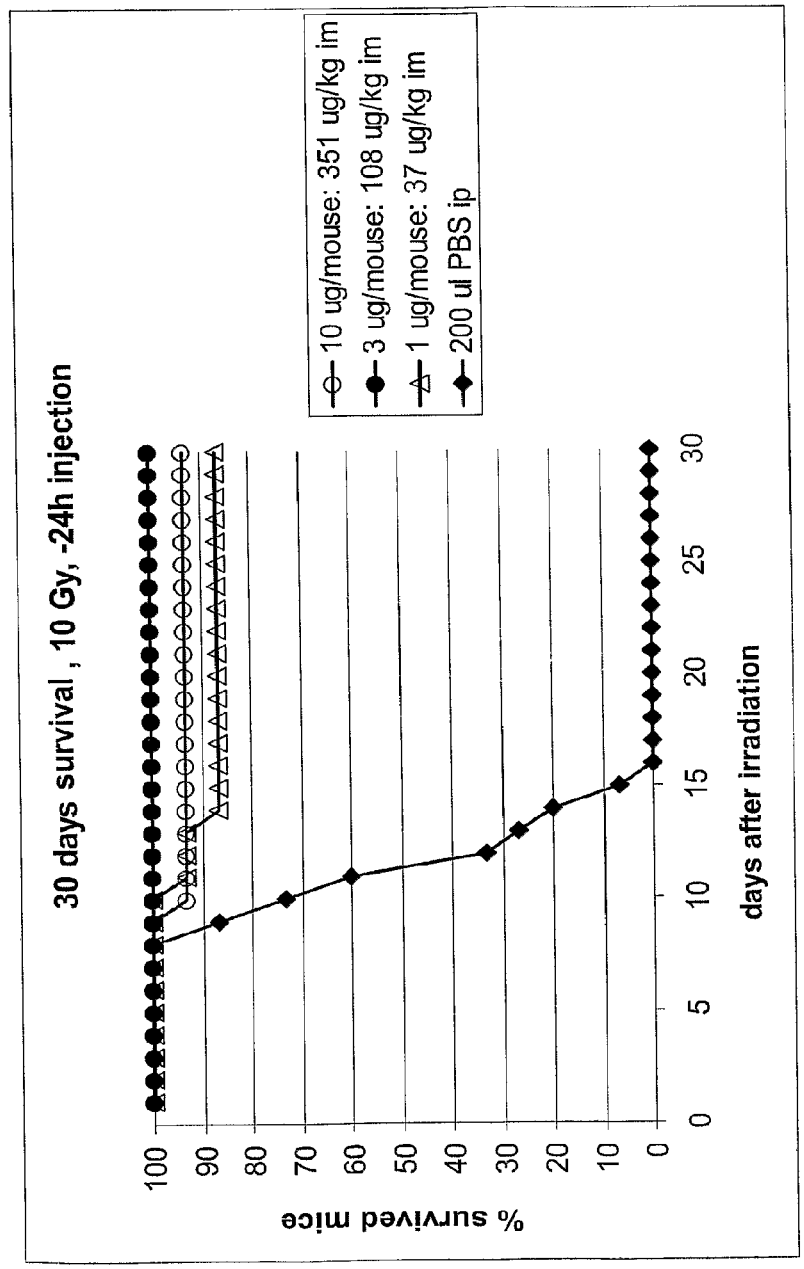
FIG. 8 illustrates the radioprotective effect of intramuscular administration of CBLB601. Shown is a graph of the percent survival of mice exposed to 10 Gy of TBI following intraperitoneal administration of PBS or intramuscular administration of 1, 3, or 10 μg of CBLB601/mouse 24 hr prior to irradiation.
Figure 9:
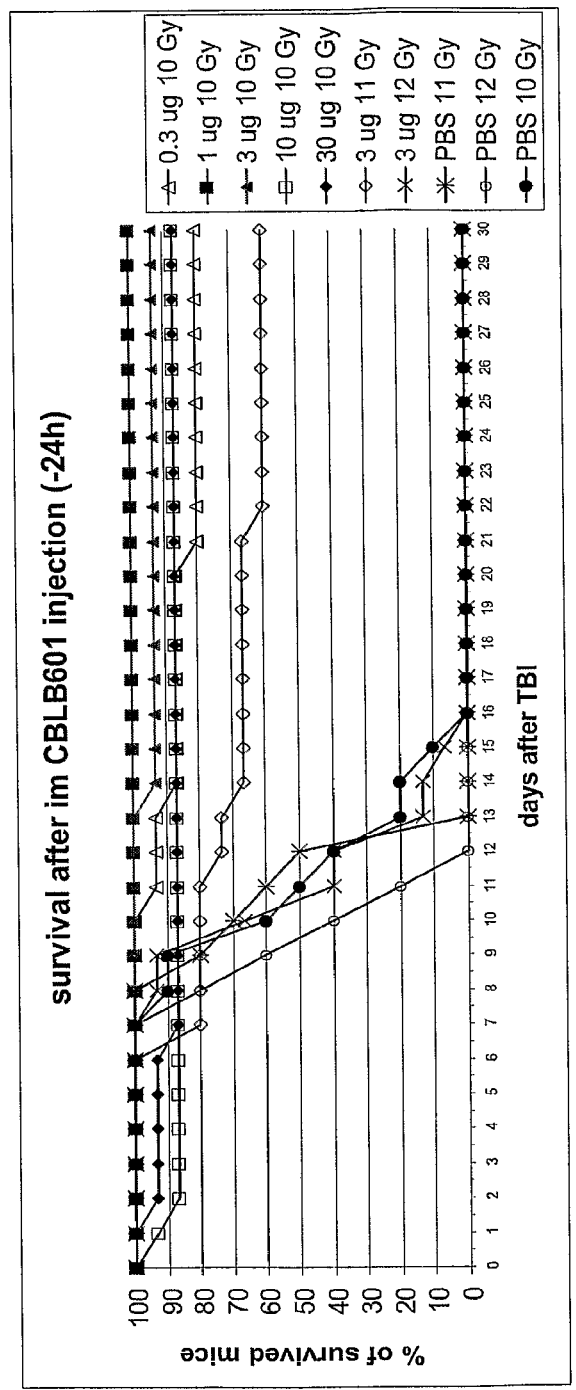
FIG. 9 depicts survival after different doses of radiation and different doses of CBLB601. Shown is a graph of the percent survival of mice exposed to 10, 11, or 12 Gy of TBI following or intramuscular administration of PBS or 0.3, 1, 3, 10 or 30 μg of CBLB601/mouse 24 hr prior to irradiation.
Figure 10:
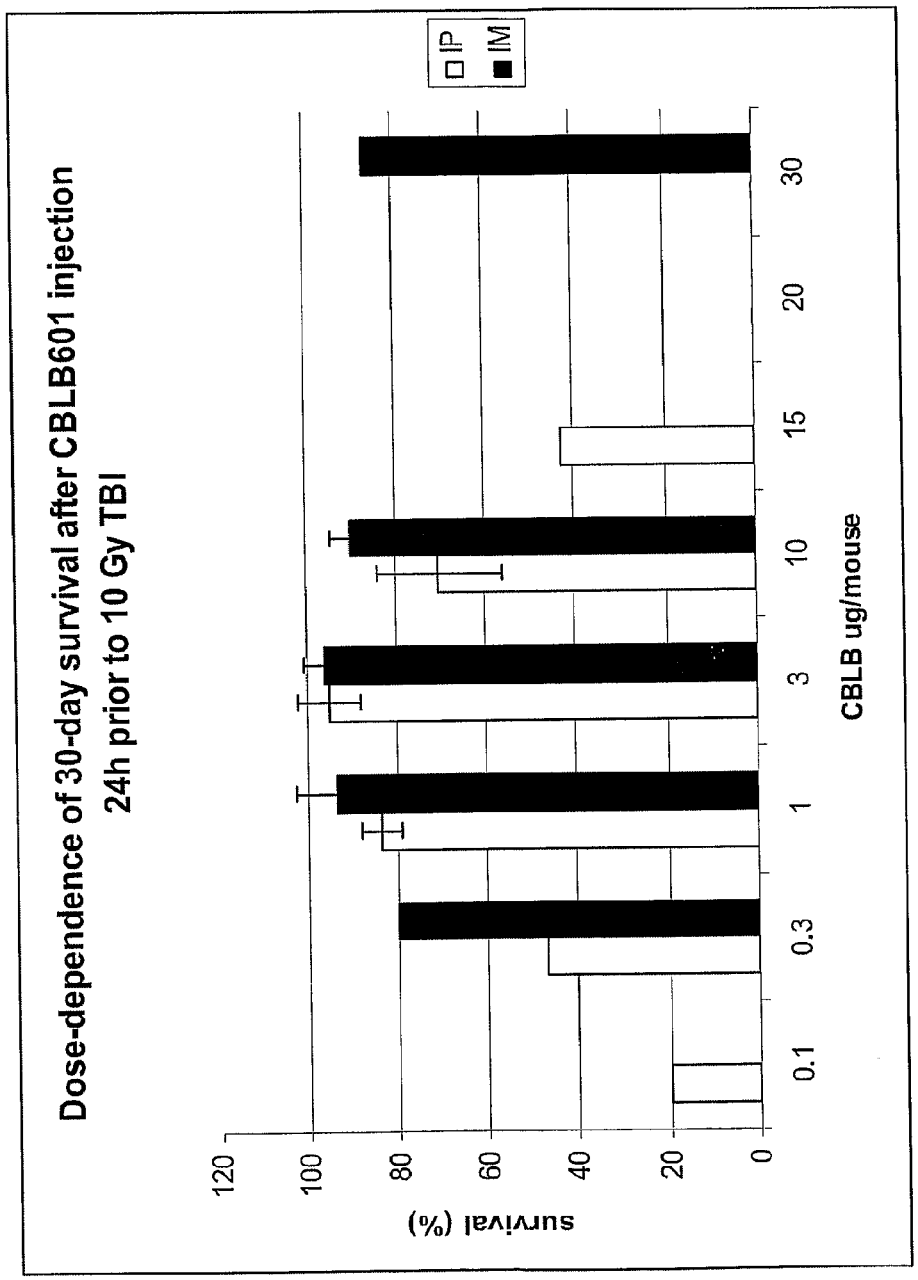
FIG. 10 compares survival after different doses of CBLB601 were administered via different routes. Shown is a bar graph of the percent survival of mice exposed to 10 Gy of TBI following intraperitoneal or intramuscular administration of different doses of CBLB601 24 hr prior to irradiation.
Figure 11:
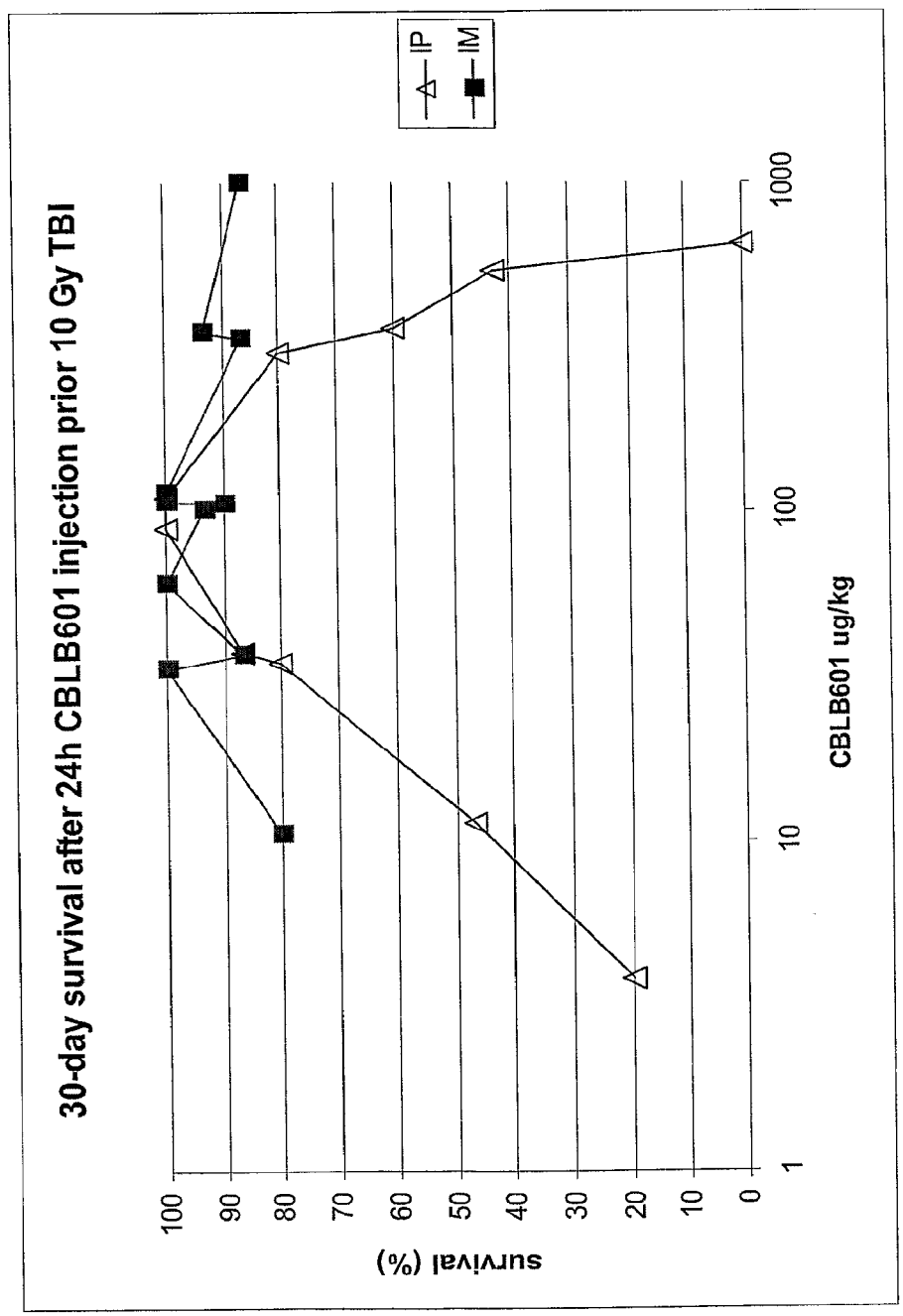
FIG. 11 compares survival after different doses of CBLB601, expressed as μg/kg, were administered via different routes. Shown is a graph of the percent survival of mice exposed to 10 Gy of TBI following intraperitoneal or intramuscular administration of different doses of CBLB601 24 hr prior to irradiation.

CBLB601 was administered intramuscularly to determine the optimal route of administration of this compound (especially since this would be the preferred route of administration for humans). FIG. 8 shows the survival rates of mice injected intramuscularly (i.m.) with 1, 3, or 10 μg of CBLB601/mouse 24 hr before irradiation. All three doses of CBLB601 imparted radioprotection; and there was no sign of combined toxicity at the 10 μg/mouse i.m. dose, as there was for the 10 μg/mouse i.p. dose (FIG. 6). In another experiment, increasing doses of CBLB601 administered i.m. were tested against 10, 11, and 12 Gy doses of HBI (FIG. 9). There was a non-statistically significant shift to increased mortality of mice injected with the higher doses (10, 30 ng) of CBLB601 prior to exposure to 10 Gy of TBI. A summary of the dose-dependency of the radioprotection of CBLB610 administered i.p. or i.m. 24 h prior to 10 Gy of TBI is shown in FIG. 10. From these data, it was concluded that the i.m. route of administration was as effective as the i.p. route, and the optimal dose (3 ng/mouse) was the same for both routes of administration. Moreover, it was concluded that i.m. delivery may be safer because it had a higher therapeutic index (toxic dose/effective dose): 10-30 for i.m. administration (FIGS. 8 and 9: 30 ng/mouse/1-2 ng/mouse) vs. 3-10 for i.p. administration (FIG. 6: 10 ng/mouse/1-3 ng/mouse). Additionally, recalculation of the effective dose per body weight revealed a smaller window for intraperitoneal delivery compared to intramuscular delivery; i.e., 90-110 ng/kg for i.p. delivery and 60-115 ng/kg for i.m. delivery (FIG. 11).

Figure 12A:
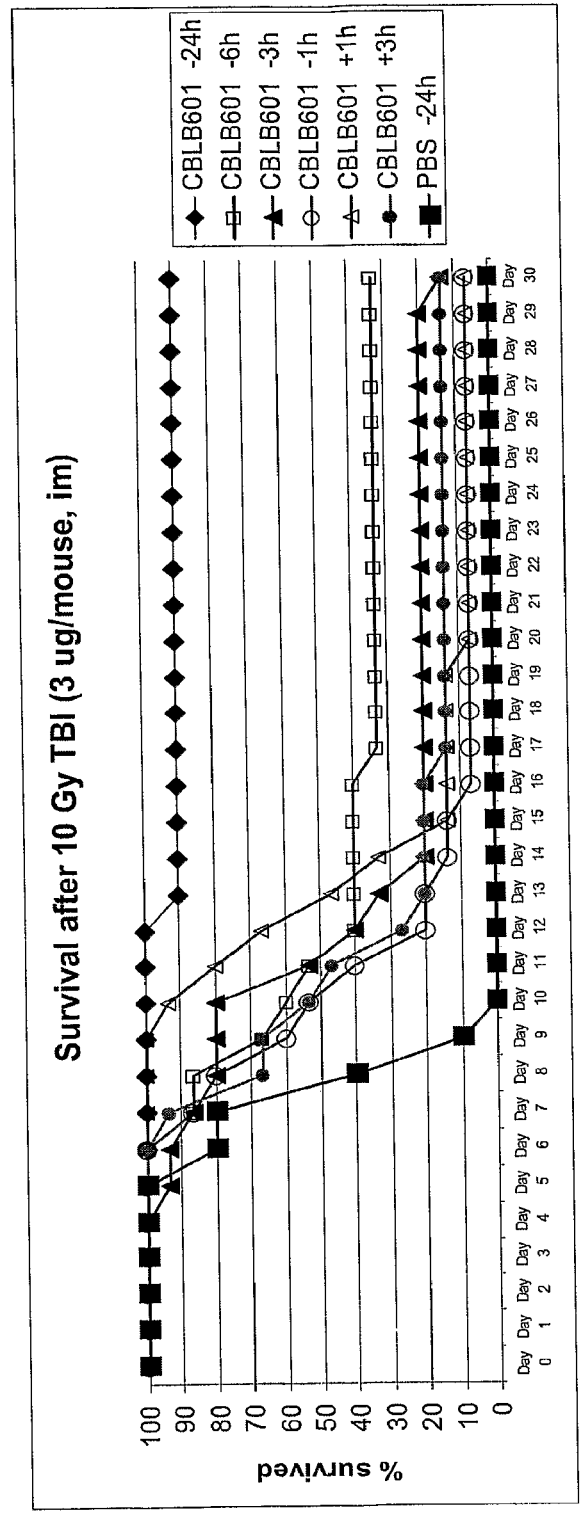
FIG. 12a shows a graph of the percent survival of mice exposed to 10 Gy of TBI following intramuscular administration of PBS or 3 μg of CBLB601/mouse 24, 6, 3, or 1 hr prior to irradiation or 1 or 3 hr after irradiation. PaB
Figure 12B:
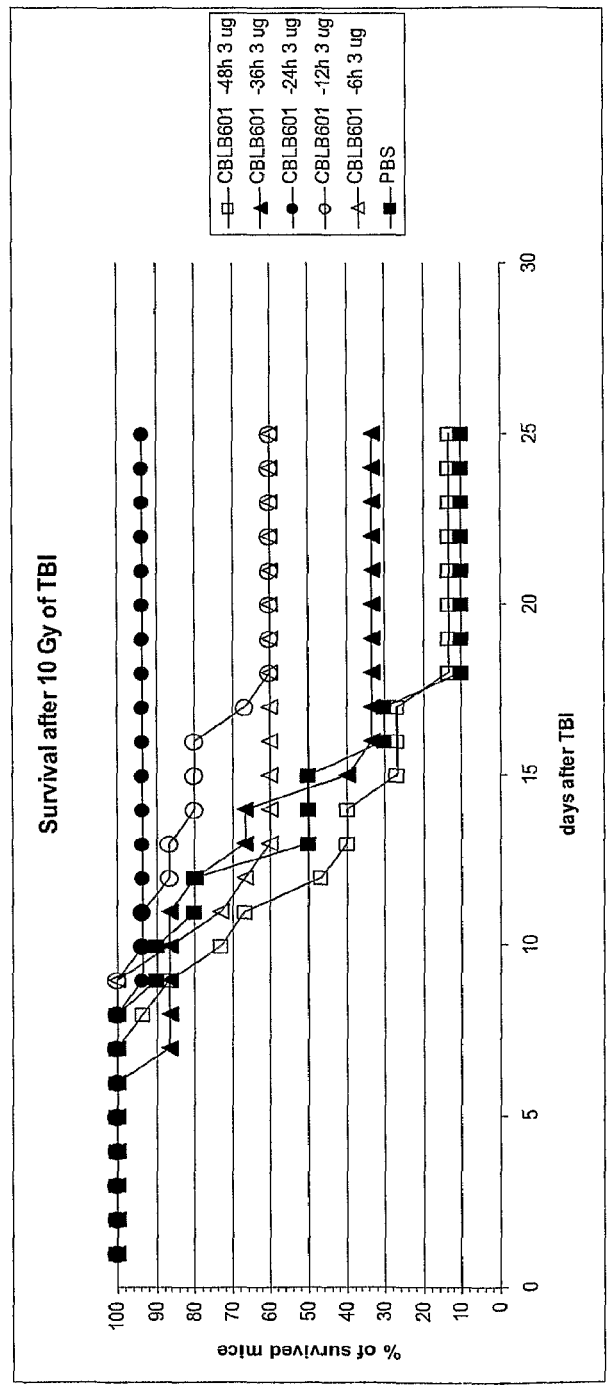
FIG. 12b shows a graph of the percent survival of mice exposed to 10 Gy of TBI following intramuscular administration of PBS or 3 μg of CBLB601/mouse 48, 36, 24, 12, or 6 hr prior to irradiation. Panel C
Figure 12C:
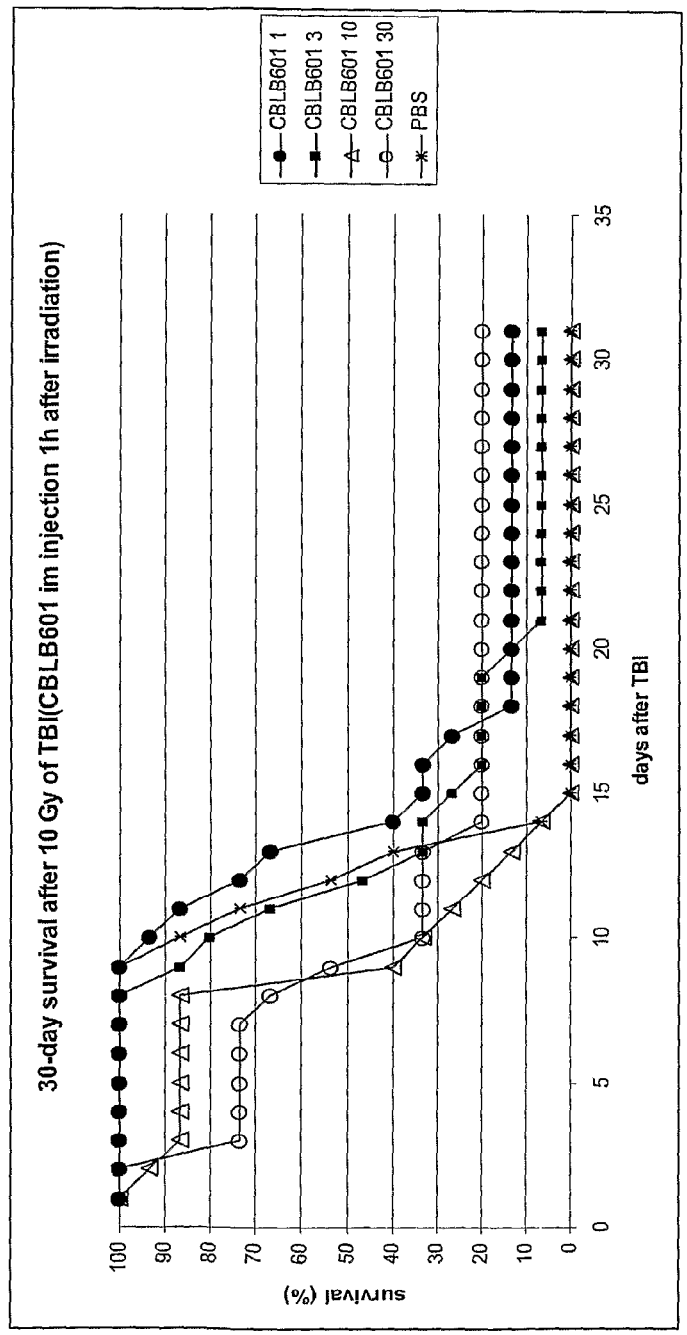
FIG. 12c shows a graph of the percent survival of mice exposed to 10 Gy of TBI following intramuscular administration of PBS or 1, 3, 10, or 30 μg of CBLB601/mouse 1 hr after irradiation.
Figure 13:
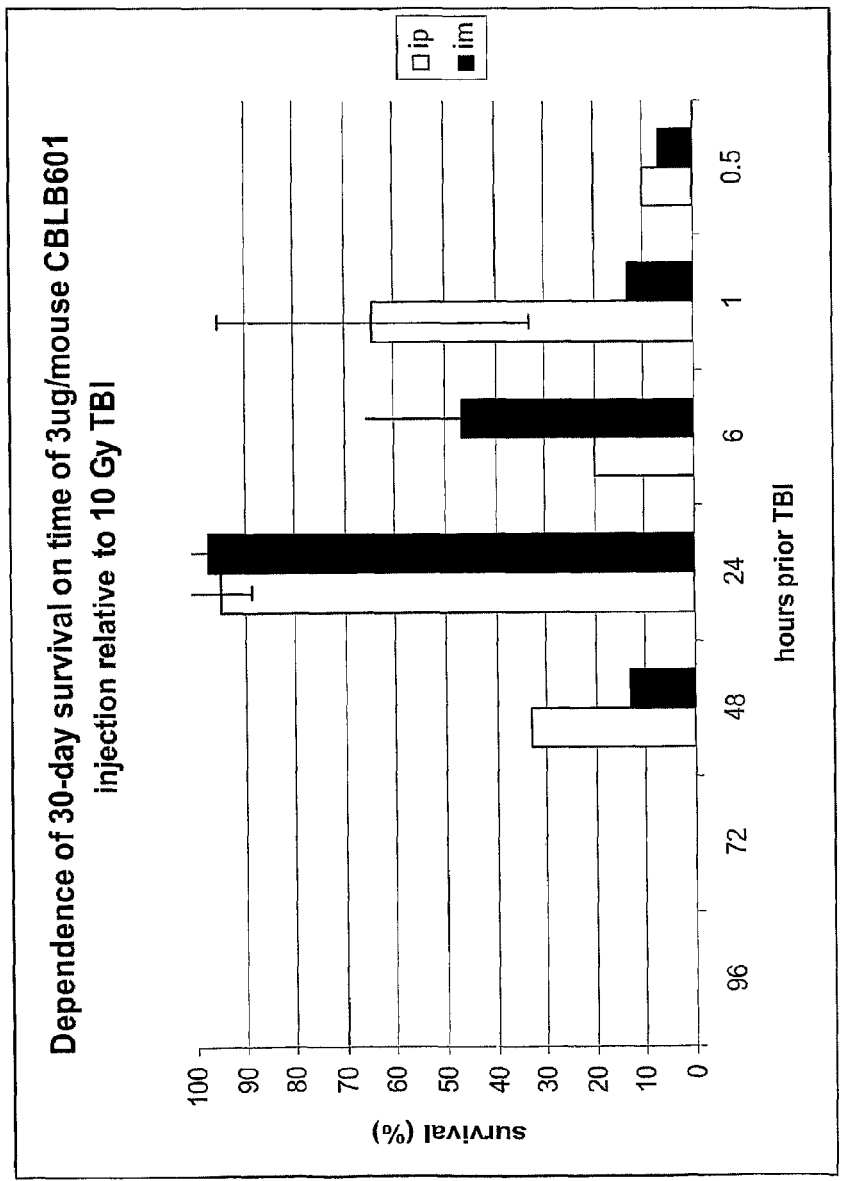
FIG. 13 compares survival as a function of the time of administration and route of administration of CBLB601. Shown is a bar graph of the percent survival of mice exposed to 10 Gy of TBI following intraperitoneal or intramuscular administration of 3 μg of CBLB601/mouse at various times prior to irradiation.

The optimal schedule of intramuscular administration of CBLB601 was determined by varying the time between drug delivery and irradiation. ICR mice were injected i.m. with 3 ng of CBLB601/mouse 24 h, 6 h, 3 h, and 1 h prior to TBI and +1 h, +3 h after TBI (FIG. 12A), as well as 48 h, 36 h, 24 h, 12 h, and 6 h prior to TBI (FIG. 12B). These experiments revealed that, similar to the intraperitoneal route of delivery, the optimal time for intramuscular delivery of CBLB601 was 24 h prior to 10 Gy of TBI. Intramuscular administration of 3 ng of CBLB610/mouse after (1 h and 3 h) 10 Gy of TBI had no protective effect (FIG. 12A). Moreover, higher doses of CBLB601 (10 and 30 ng/mouse) injected i.m. 1 h after 10 Gy of TBI caused increased levels of combined toxicity (FIG. 13C). These data are summarized in FIG. 13.

Figure 14:
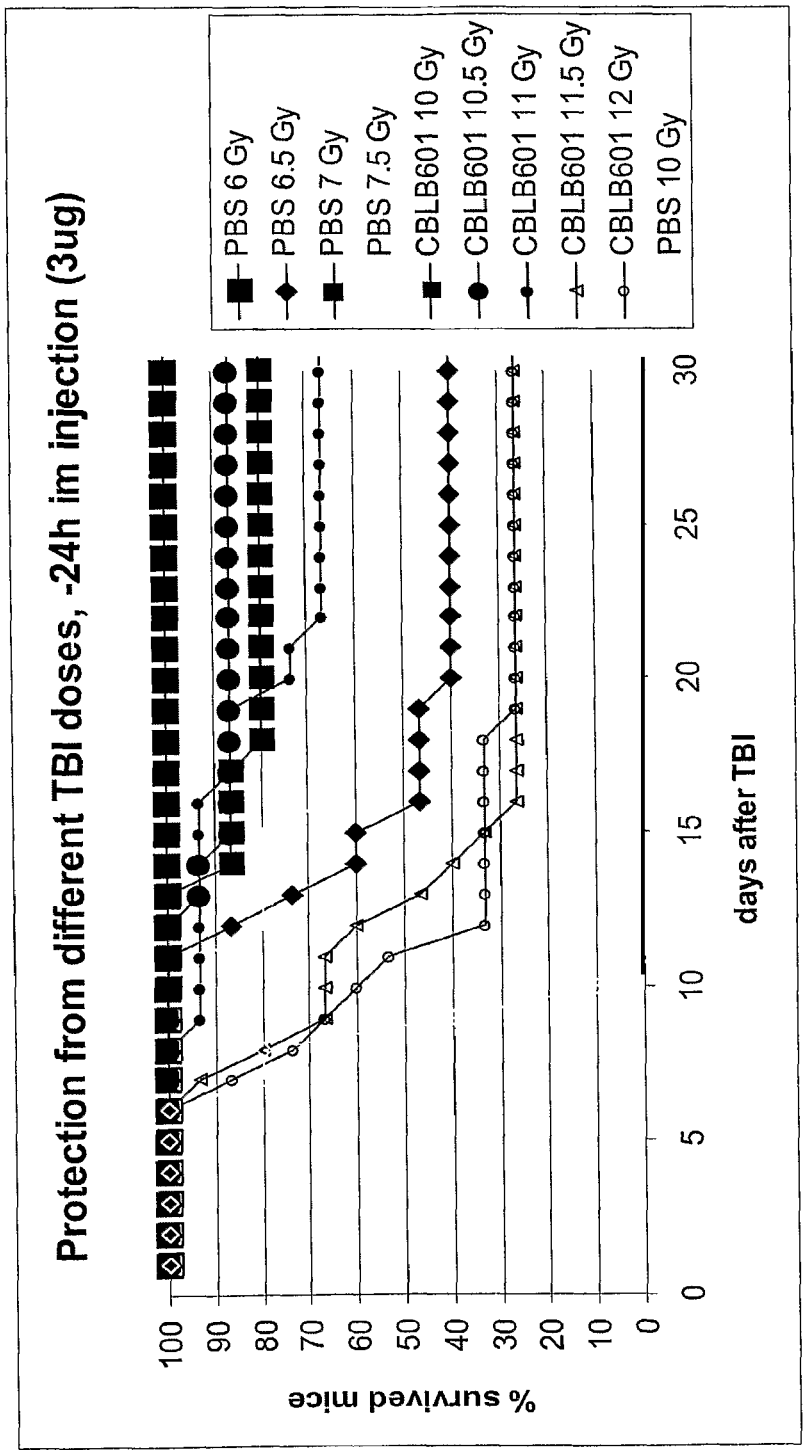
FIG. 14 illustrates the determination of the Dose Modification Factor at day 30 ($DMF_{30}$) for CBLB601 under the optimal radioprotective conditions. Shown is a graph of the percent survival of mice exposed to various doses of radiation following intramuscular administration of PBS or 3 μg of CBLB601/mouse 24 hr prior to irradiation.

To determine DMF (dose modification factor), 3 ng of CBLB601/mouse was injected i.m. 24 hr prior to irradiation and control mice were injected with PBS. Both drug-injected and control groups received a single dose of TBI covering the dose range that leads to 10-90% mortality within the chosen time intervals (7 days for the gastrointestinal syndrome mortality, and 30 days for the hematopoietic syndrome mortality). The percent mortality-radiation dose graphs were built and $LD_{50/7}$ and $LD_{50/30}$ ($LD_{50}$ at 7 days and 30 days, respectively) were calculated using probit or logit statistical analysis. DMF (also known as dose reduction factor, DRF) was calculated as a ratio of radiation $LD_{50}$ for CBLB601-treated groups and radiation $LD_{50}$ for vehicle-treated groups of mice for the chosen survival time point, 7 or 30 days. To calculate $DMF_{30}$, which is the DMF at day 30 post-irradiation, the radiation $LD_{50/30}$) values for mice treated with PBS or 3 ng of CBLB601 was determined. For this, PBS-injected groups were irradiated with doses of 6, 6.5, 7, and 7.7 Gy of TBI, and CBLB601-injected groups were irradiated with doses of 10, 10.5, 11, 11.5, and 12 Gy of TBI. The $LD_{50/30}$ for CBLB601 was calculated using ProBit analysis and was estimated to be in the range of 11.07-11.61Gy, with the average of ~11.32 Gy (see FIG. 14). However, inconsistency in the response to some radiation doses (7 Gy appeared non-toxic whereas 6.5 Gy caused 60% lethality at 30 days) in the control mice precluded an accurate calculation of the $DMF_{30}$ for CBLB601. Nevertheless, it was expected that the $LD_{50/30}$ for ICR mice was around 7 Gy [an average for the majority of mouse strains; Monobe et al., Radiother Oncology 73 Suppl 2: 512709, 2004)]. Thus, the value of $DMF_{30}$ for CBLB601 was estimated roughly as ~1.6.

Example 4

Immune Status of Mice Rescued from Lethal Doses of TBI by CBLB601

Figure 15:
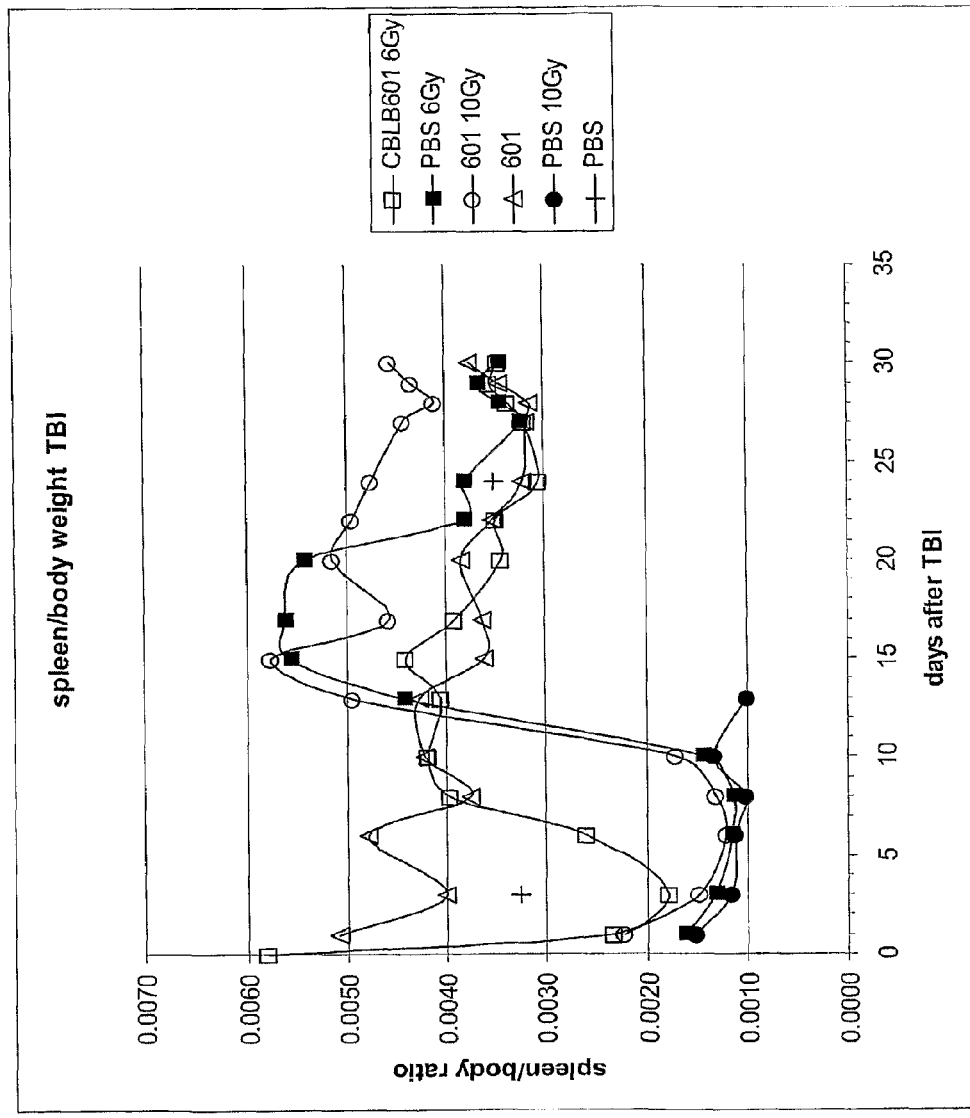
FIG. 15 presents a graph of the average weights of spleens from irradiated control and CBLB601-treated mice. Plotted is the spleen weight per body weight ratio for mice exposed to 0, 6, or 10 Gy of TBI following intramuscular administration of PBS or 3 µg of CBLB601/mouse 24 hr prior to irradiation.

Mice that have been rescued from 10 Gy of TBI by administration of CBLB601 may have compromised immune systems, and hence, may not have "normal" lives. To check the status of their immune systems, ICR mice were exposed to lethal (10 Gy) or non-lethal (6 Gy) doses of TBI 24 hr after they had been injected (i.m.) with 3 ng CBLB601/mouse or PBS. Groups of five mice from each condition were sacrificed very three days and their spleens and thymuses were removed and weighed. The weights of the spleens were normalized to the body weights of the corresponding animals and the results are presented in FIG. 15. PBS-treated mice that were exposed to 6 Gy of radiation took about 13-14 days to restore their spleens to normal weights, whereas CBLB601-treated mice exposed to 6 Gy of radiation had normal spleen weights by day 8. PBS-injected animals did not survive 10 Gy of TBI, whereas CBLB601-injected mice not only survived the lethal dose of radiation, but also completely restored their spleen weights by day 13-14 post irradiation. It took a longer period of time (~30 days) to restore the thymuses to normal weights (not shown).

The spleens and thymuses from control and CBLB601-injected mice were examined microscopically for morphological changes at 3, 10 and 30 days after irradiation. At 3 days post-irradiation, the spleen and thymus of 10 Gy whole body irradiated control and CBLB601-treated mice revealed irradiation-induced lesions, including moderately severe or severe lymphoid depletion of the spleen and thymus, and severe red pulp atrophy of the spleen. At 10 days post-irradiation, CBLB601-treated animals showed an improvement over the control animals in recovery from splenic red pulp atrophy; all CBLB601-treated animals showed mild to moderate multifocal extramedullary hematopoiesis (EMH) whereas none of the controls displayed EMH. There was no evidence of recovery of the splenic white pulp depletion in either group at day 10. Regenerative lymphoid hyperplasia in the thymus was evident in both groups at day 10, with the regeneration slightly more advanced in the control that in the CBLB601-treated mice. By day 30 post-irradiation, all animals had normal splenic red pulp, most animals showed full or nearly full recovery of lymphoid elements, and all had essentially normal thymuses.

To test the immune response of mice rescued from a lethal dose of gamma-irradiation (10 Gy of TBI) by CBLB601, several groups of such mice were subjected to immunization with a strong antigen, *Salmonella flagellin*. The mice were first immunized at 8, 18, or 20 weeks after irradiation, at which time they were 18, 25, and 33 weeks of age, respectively. Non-irradiated naïve mice at 29 weeks of age were used as a positive control for the immune response. The mice received a boost of flagellin one week after the first immunization, and another boost three weeks after the $2^{nd}$ boost; anti-flagellin antibody titers were measured in mouse serum. To test the secondary immune response, the mice were bled again a month later to insure reduction of the antibody titers. This was followed by a $3^{rd}$ boost of the antigen injection and measurement of anti-flagellin antibodies titers 10 days later. At the time of the $3^{rd}$ boost, the irradiation mice were 38, 30, and 23 weeks old, and the control mice were 34 weeks old.

Figure 16A:
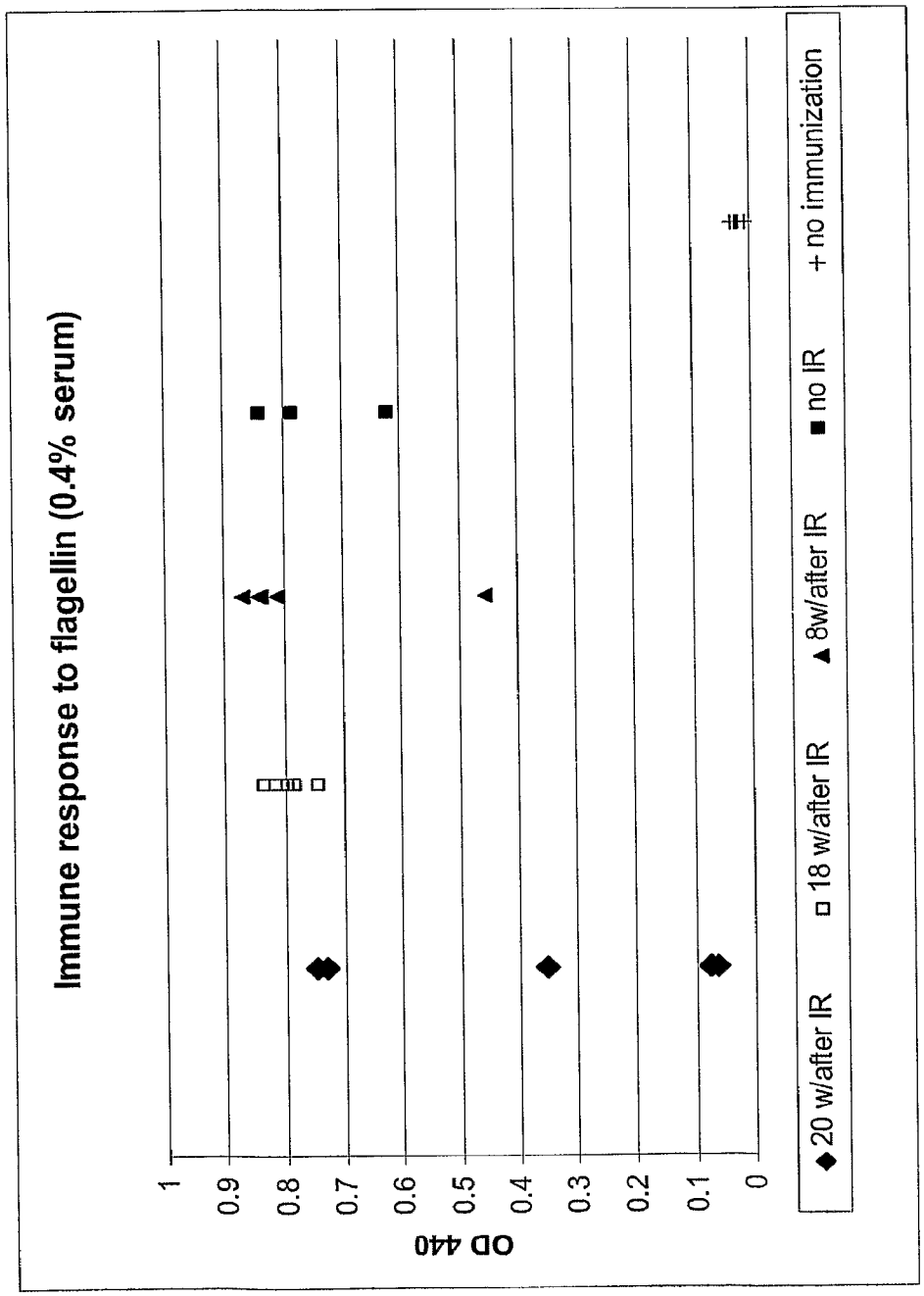
FIG. 16a shows the immune response of the different groups one month after the first immunization.
Figure 16B:
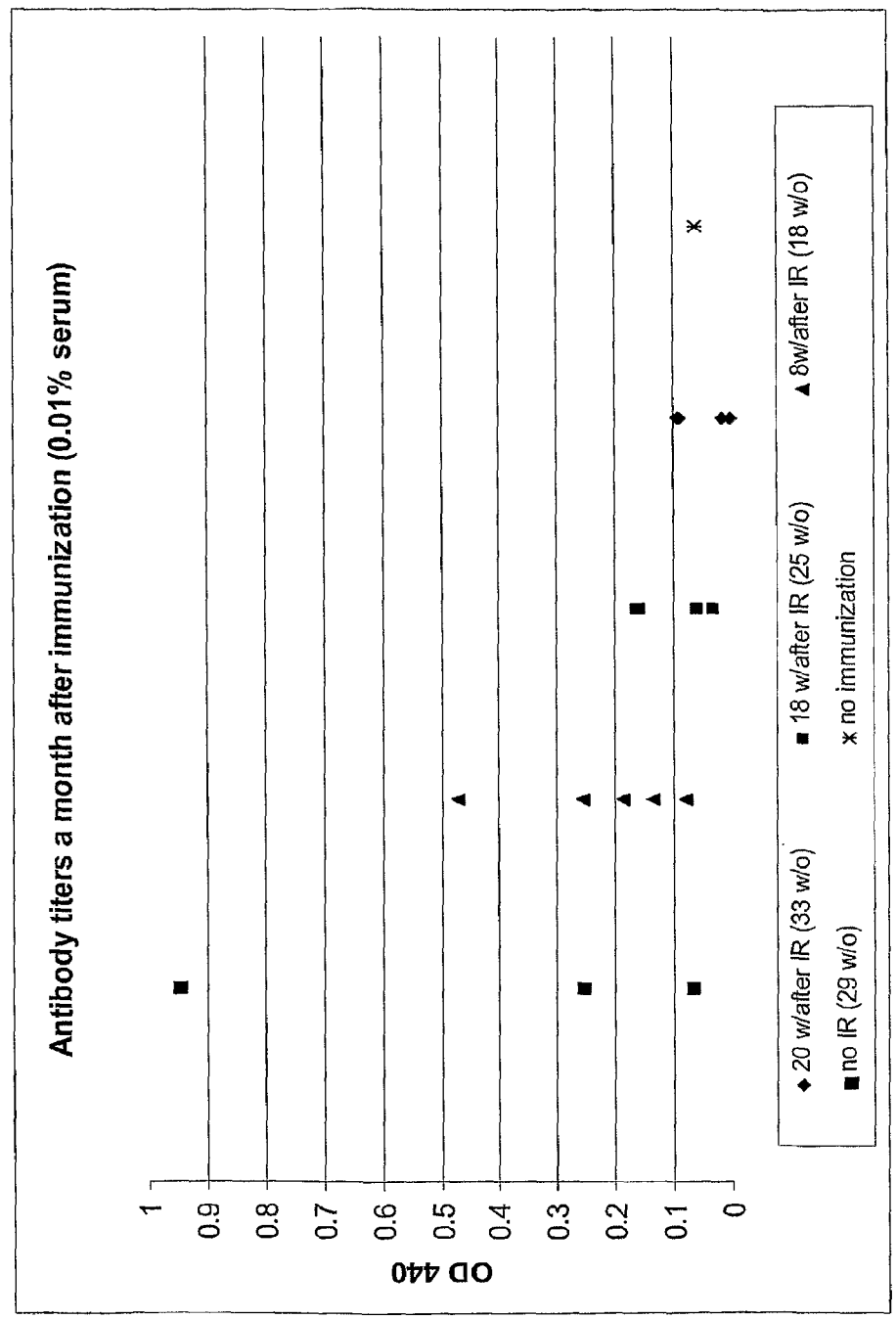
FIG. 16b shows the immune response of the different groups one month after the first bleed.
Figure 16C:
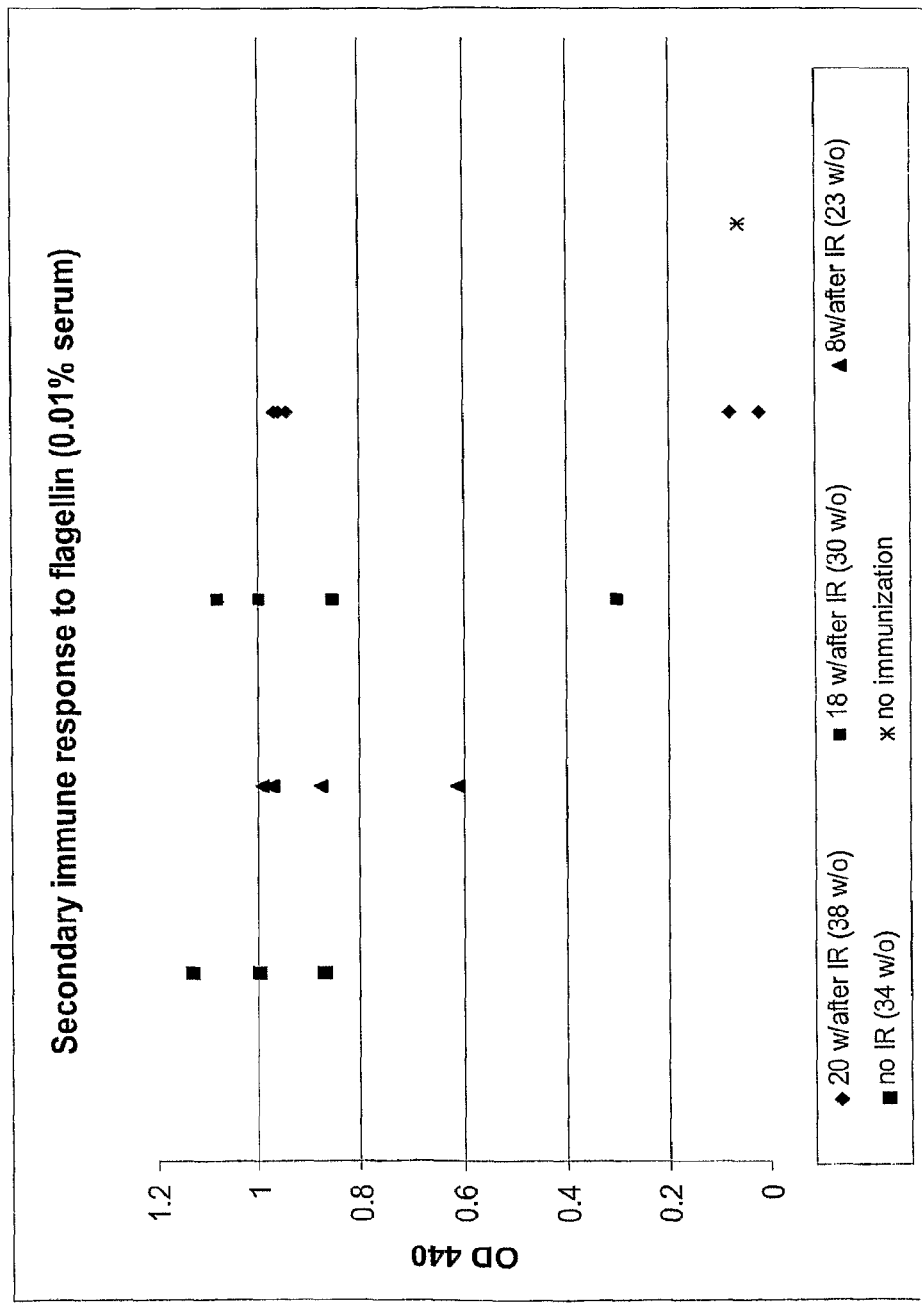
FIG. 16c shows the secondary immune response to flagellin of the different groups 10 days after the third immunization.

The immune response one month after the first immunization (three weeks after the first boost) is shown in FIG. 16A. The CBLN601-treated irradiated mice mounted a robust humoral immune response against flagellin that was indistinguishable from that of the naïve control mice. It also appears that the level of immune response was not dependent on the time that had passed after irradiation, since all groups displayed a good response. While there was some individual variation in the 20-week post-irradiation group, it is well known that immune response can be impaired in older animals. Antibody titers were checked again one month after the first bleed, and they were still elevated seven weeks after immunization (FIG. 16B). The secondary immune response (FIG. 16C) was stronger than the first response (FIG. 16A). These data strongly indicate that CBLB601 not only rescued mice from lethal TBI, but also allowed for full restoration of a functional immune system.

Example 5

Activation of NF-κB and Radioprotection Provided by Other Lipopeptides

Additional lipopeptides were synthesized and tested for activation of NF-κB and their ability to protect mice from lethal doses of radiation. The names of the compounds and their key constituents are shown in Table 4. For some of the compounds, the corresponding free peptides were also synthesized and tested.

TABLE 4

| Compound Name | N-acylation | Peptide Sequence | SEQ ID NO |
|---|---|---|---|
| CBLB602 | Pam2 | GQHHH | 12 |
| CBLB603 | Pam2 | GQHHM | 11 |
| CBLB604 | Pam2 | GSHHM | 14 |
| CBLB605 | Pam2 | SQMHH | 15 |
| CBLB606 | R-Pam2 | GDPKHPKSF | 24 |
| CBLB607 | Pam2 | GDPKHPKSFTGWVA | 32 |
| CBLB608 | Pam2 | FEPPPATTTKSK | 30 |
| CBLB611 | Pam2 | GETDKEGKIIRIFDNSF | 37 |
| CBLB612 | R-Pam2 | VQGEESNDK | 21 |
| CBLB613 | R-Pam2 | GETDK | 16 |
| CBLB614 | R-Pam2 | QGEESNDK | 20 |
| CBLB615 | R-Pam2 | GEESN | 17 |
| CBLB616 | R-Pam2 | TENVKE | 19 |
| CBLB617 | R-Pam2 | GEEDD | 18 |

Figure 17:
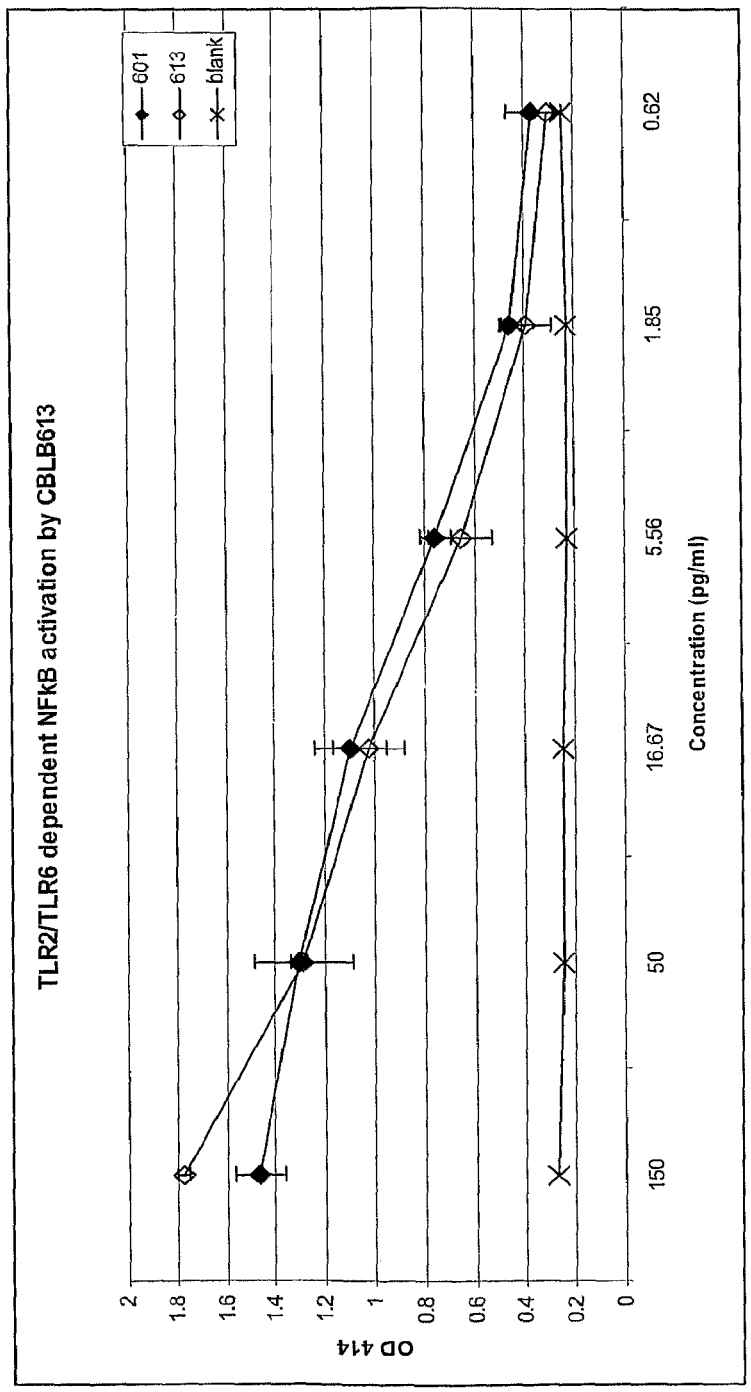
FIG. 17 is a graph of the activation of a NF-κB reporter by various doses of CBLB613 and CBLB601 in 293 cells expressing the TLR2/TLR6 heterodimer.
Figure 18A:
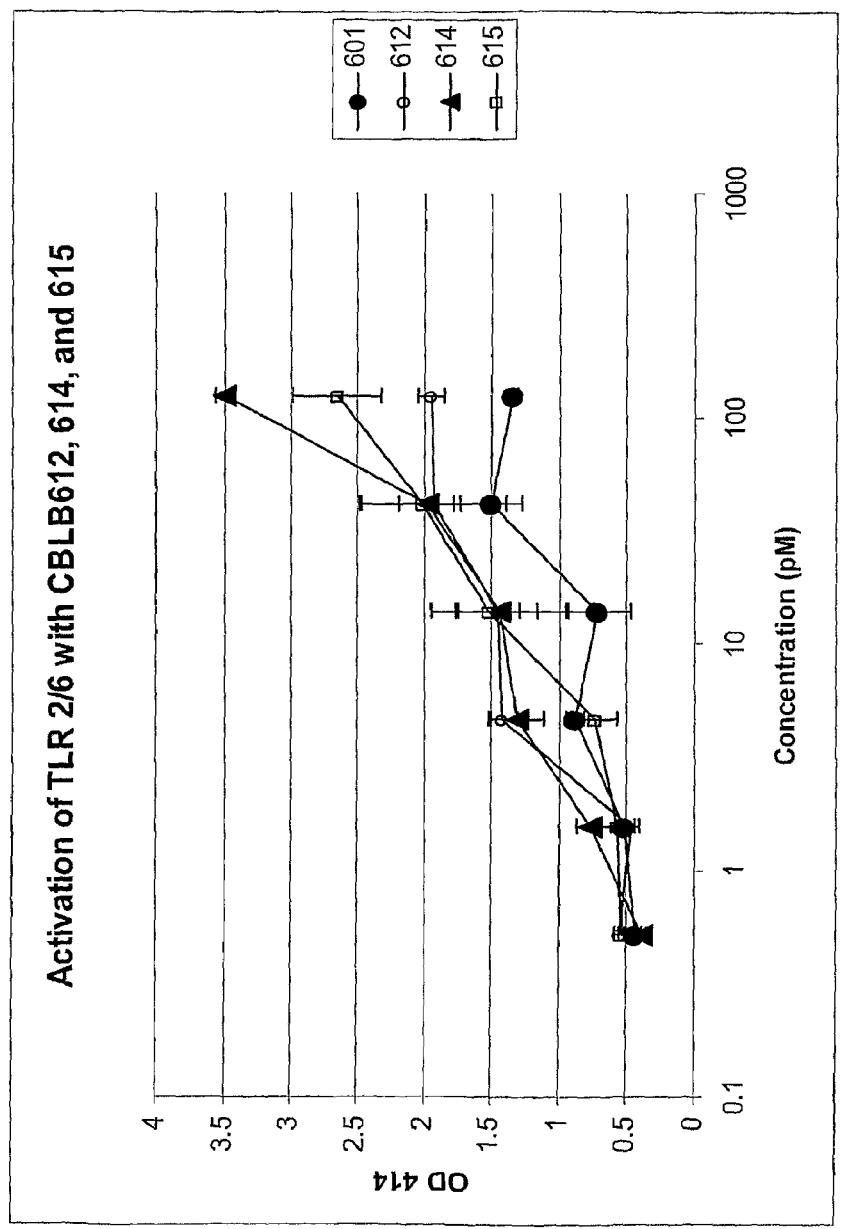
FIG. 18a presents NF-κB activation by various doses of CBLB601, CBLB612, CBLB614, or CBLB615.
Figure 18B:
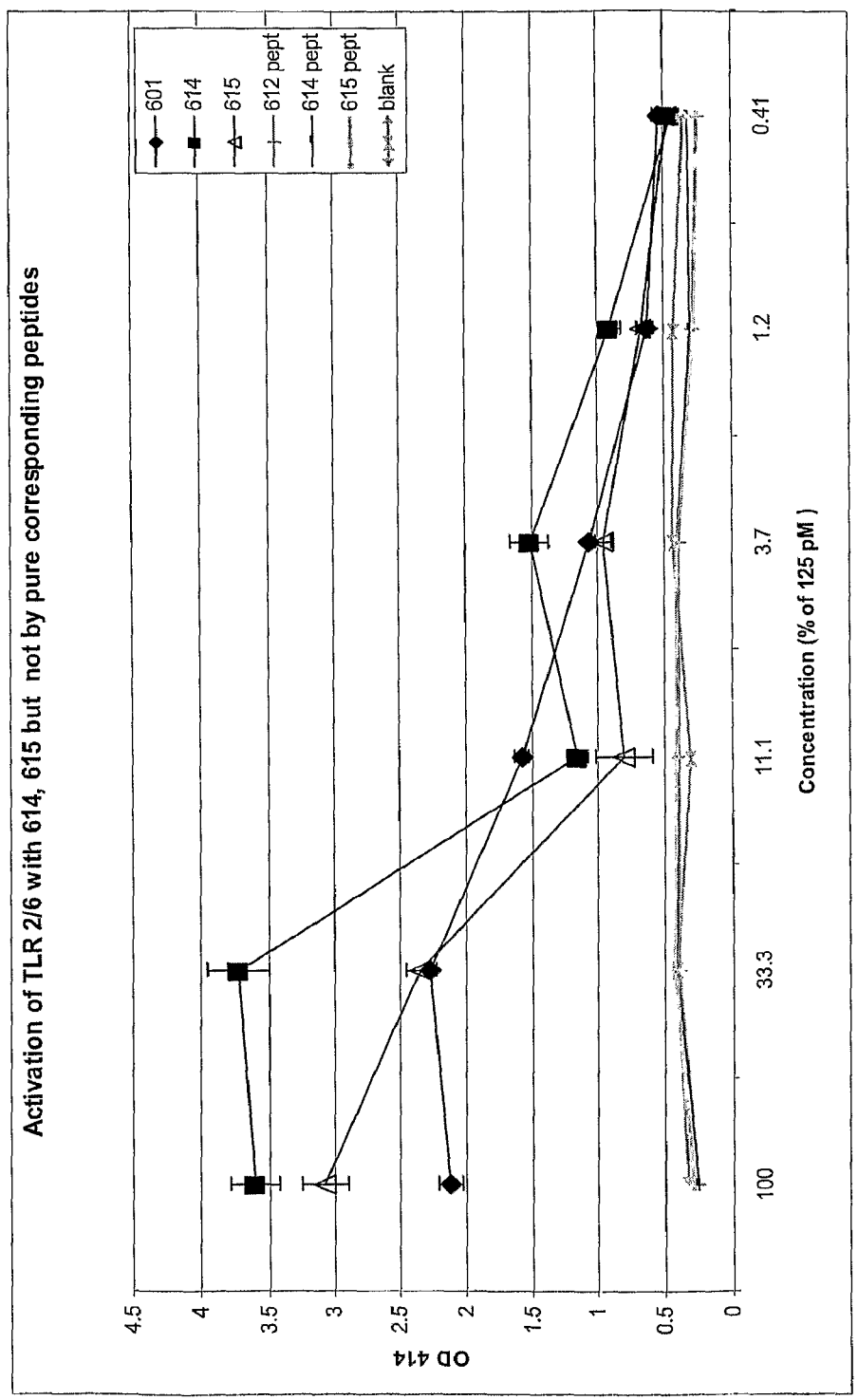
FIG. 18b presents NF-κB activation by various doses of CBLB601, CBLB612, CBLB614, or CBLB615, and no activation by the corresponding free peptides.
Figure 19:
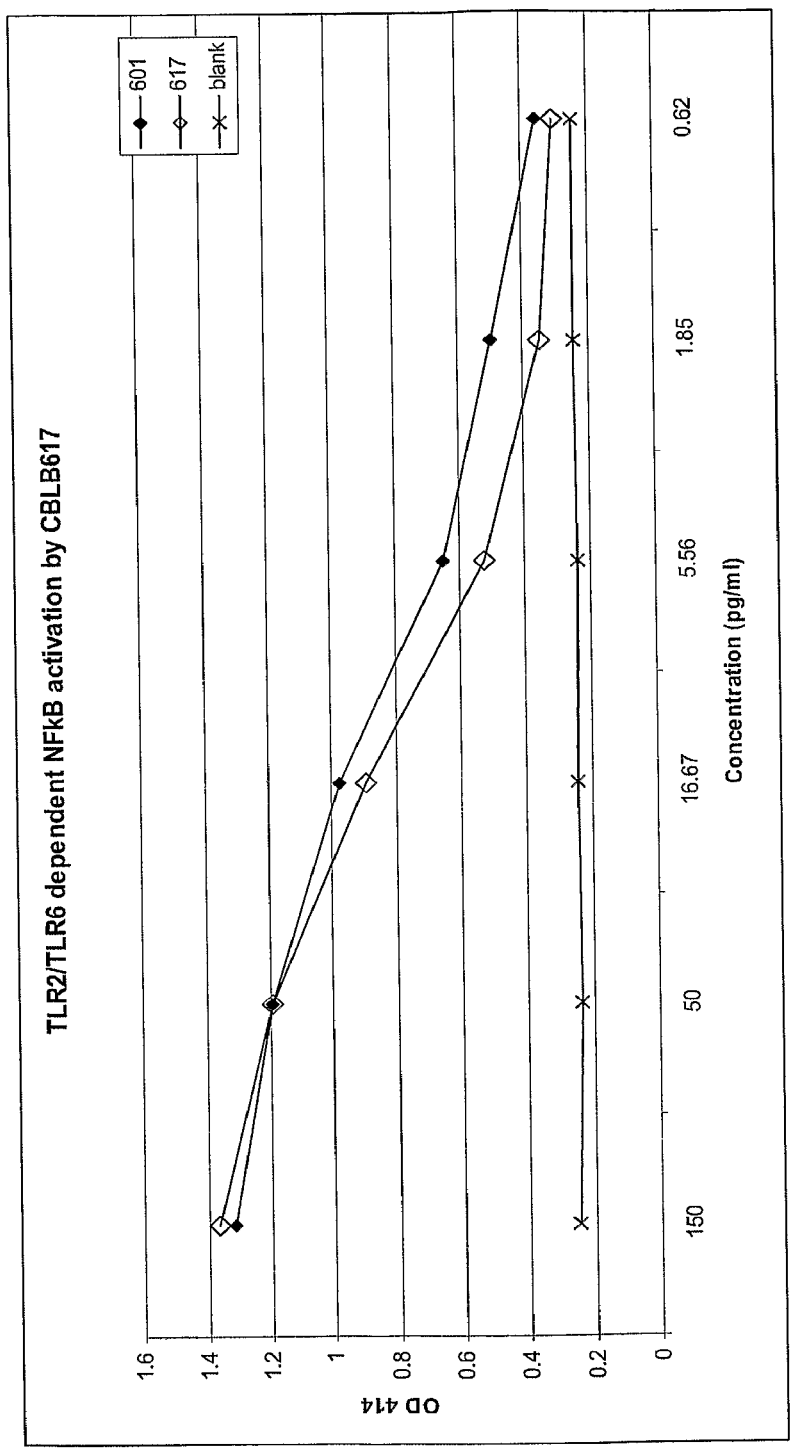
FIG. 19 is a graph of the activation of a NF-κB reporter by various doses of CBLB617 and CBLB601 in 293 cells expressing the TLR2/TLR6 heterodimer.

NF-κB-dependent reporter activity was measured in 293 cells that expressed the TLR2/YLR6 heterodimer. The in vitro activation of NF-κB by CBLB613 was comparable to that of CBLN601 (FIG. 17). The compounds CBLB614 and CBLB615 have successively shorter derivatives of the peptide of CBLB612 (see Table 4). All three compounds activated the NF-κB reporter, and all were better activators than CBLB601 (FIG. 18A, B). None of the non-palmitoylated corresponding peptides activated the NF-κB reporter (FIG. 18B). The peptide component of CBLB617 has a (~4) charge, which should prevent it from interacting with negatively charged cell surface markers. The NF-κB activation of CBLB617 was comparable to that of CBLB601 (FIG. 19). Table 5 summarizes the in vitro activity and solubility of all the compounds.

TABLE 5

| Coumpound | Solubility | NF-κB activation |
|---|---|---|
| CBLB601 | Excellent | 100 |
| CBLB602 | Poor | 0 |
| CBLB603 | Poor | 0 |
| CBLB604 | Poor | 0 |
| CBLB605 | Poor | 2 |
| CBLB606 | Poor | 100 |
| CBLB607 | Poor | 2 |
| CBLB608 | Excellent | 2 |
| CBLB611 | Insoluble | 0 |
| CBLB612 | Excellent | 200 |
| CBLB613 | Soluble | 200 |
| CBLB614 | Soluble | 200 |
| CBLB615 | Soluble | 200 |
| CBLB616 | Not tested | Not tested |
| CBLB617 | Soluble | 100 |

The in vivo radioprotective activity of some of the compounds was also tested. ICR mice were injected intramuscularly with various doses of the test compounds and then 24 hours later the mice were exposed to 10 Gy of TBI. Survival was monitored for 30 days.

Figure 20:
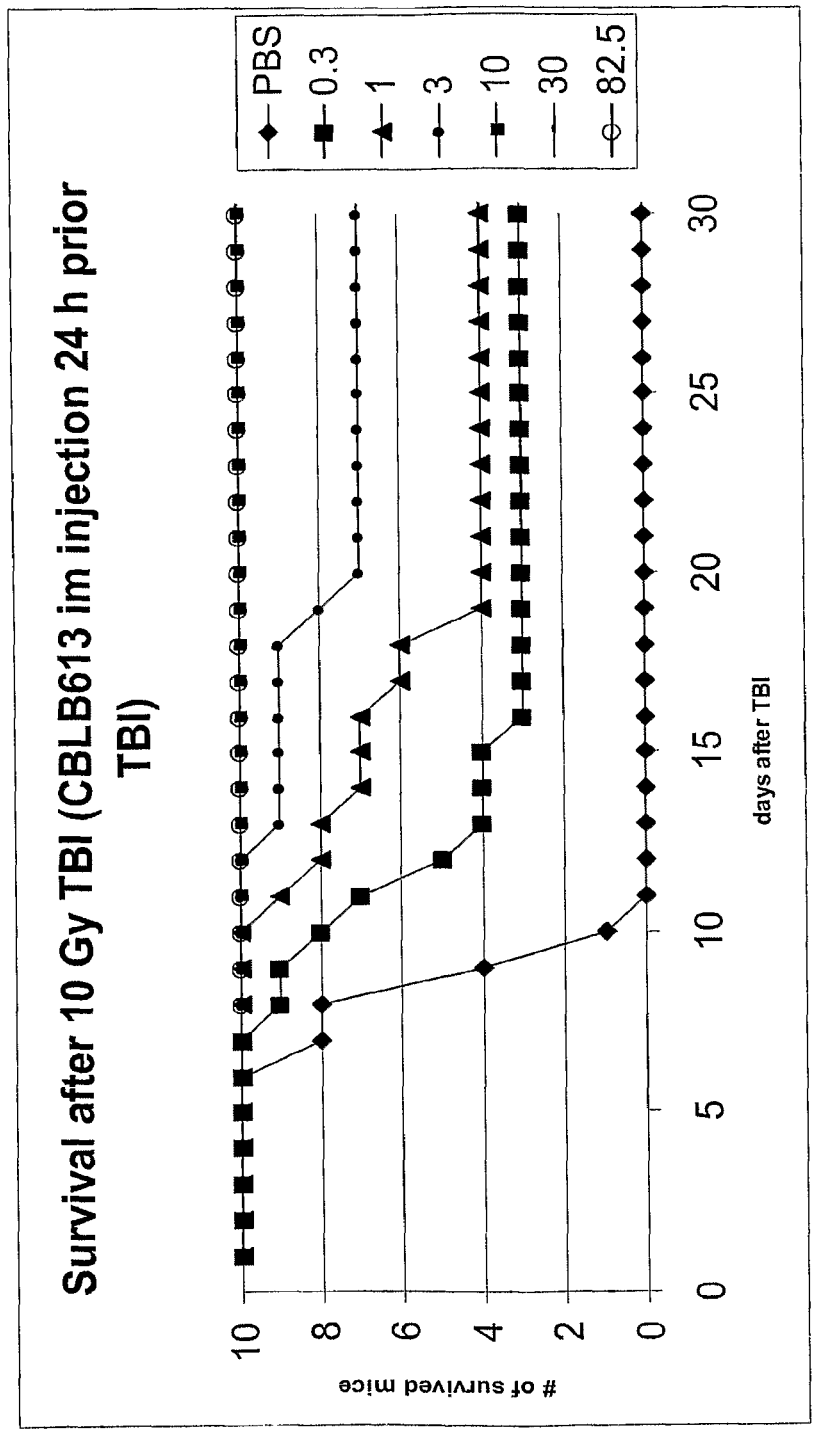
FIG. 20 illustrates the radioprotective activity of CBLB613. Shown is a graph of the percent survival of mice exposed to 10 Gy of TBI following intramuscular administration of PBS or 0.3, 1, 3, 10, 30, or 82.5 µg of CBLB613/mouse 24 hr prior to irradiation.
Figure 21:
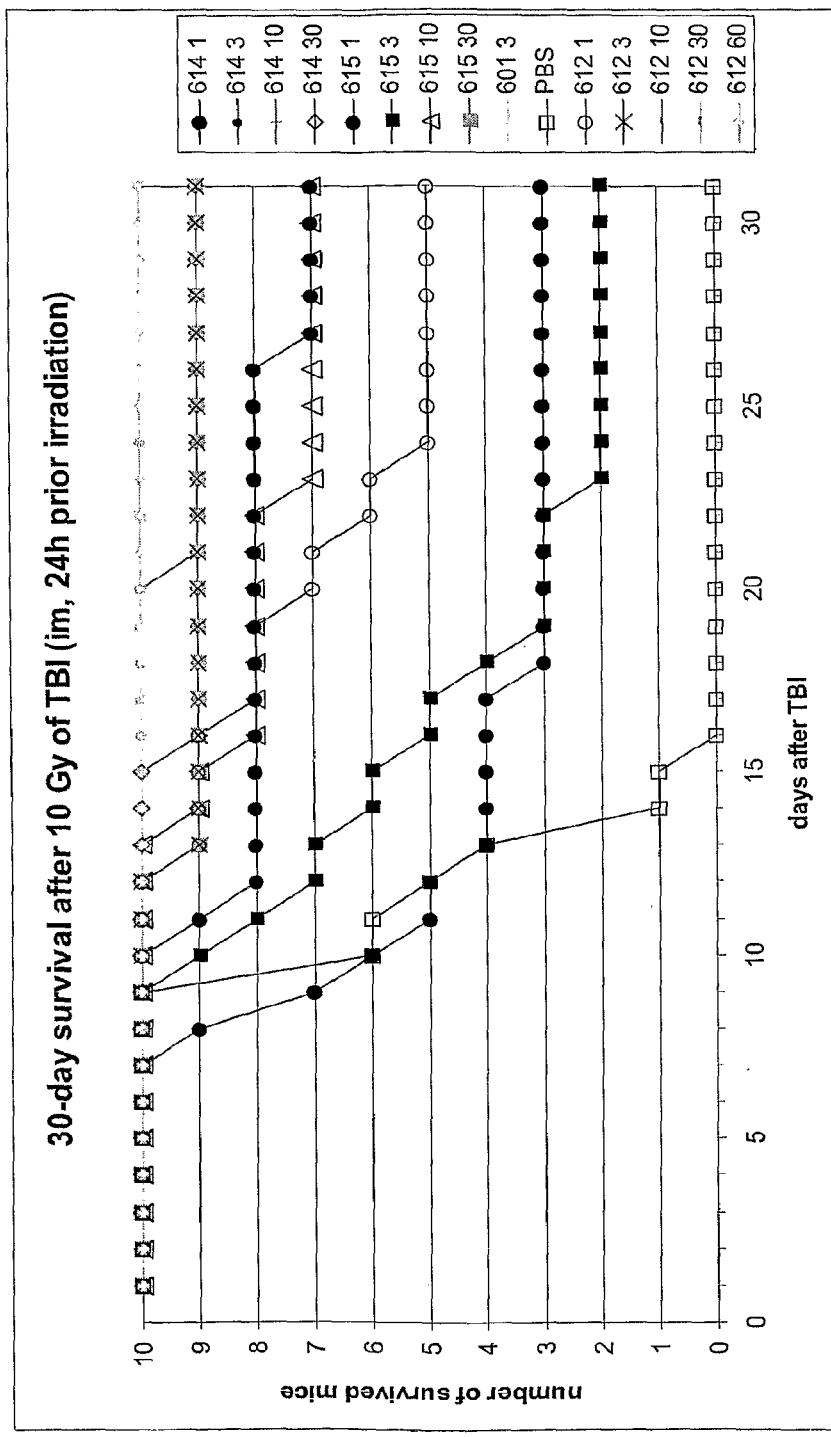
FIG. 21 illustrates the radioprotective activity of CBLB612, CBLB614, and CBLB615. Shown is a graph of the percent survival of mice exposed to 10 Gy of TBI following intramuscular administration of PBS or various doses of CBLB612, CBLB614, or CBLB615 24 hr prior to irradiation.

FIG. 20 shows the protective activity of CBLB613. Doses of 10, 30, and 82.5 μg of CBLB613/mouse provided 100% protection, and were non-toxic in combination with the radiation (in contrast to CBLB601). The related compounds, CBLB612, CBLB614, and CBLB615 were tested for radioprotective activity against 10 Gy of TBI. Doses of 1, 3, 10, and 30 μg/mouse (CBLB612 was also tested at 60 μg/mouse) were injected i.m. into ICR mice 24 hrs before irradiation. As shown in FIG. 21, all three of the compounds provided 90-100% radioprotection when administered at the highest doses. The radioprotection was clear dose-dependent, with no toxicity in combination with radiation. The potency of the compounds are CBLB612>CBLB614>CBLB615. The radioprotective activity of CBLB617 is currently under evaluation using the standard procedure. After 13 days, there was no visible toxicity at the highest dose (87.5 μg/mouse), while there was 7-90% survival at doses of 10-87.5 μg/mouse, respectively. In summary, CBLB612 and CBLB613 are significantly better radioprotectors than CBLB601, and they have higher therapeutic indices (~20 for CBLB612 and CBLB613 vs. 3 for CBLB601).

Figure 22:
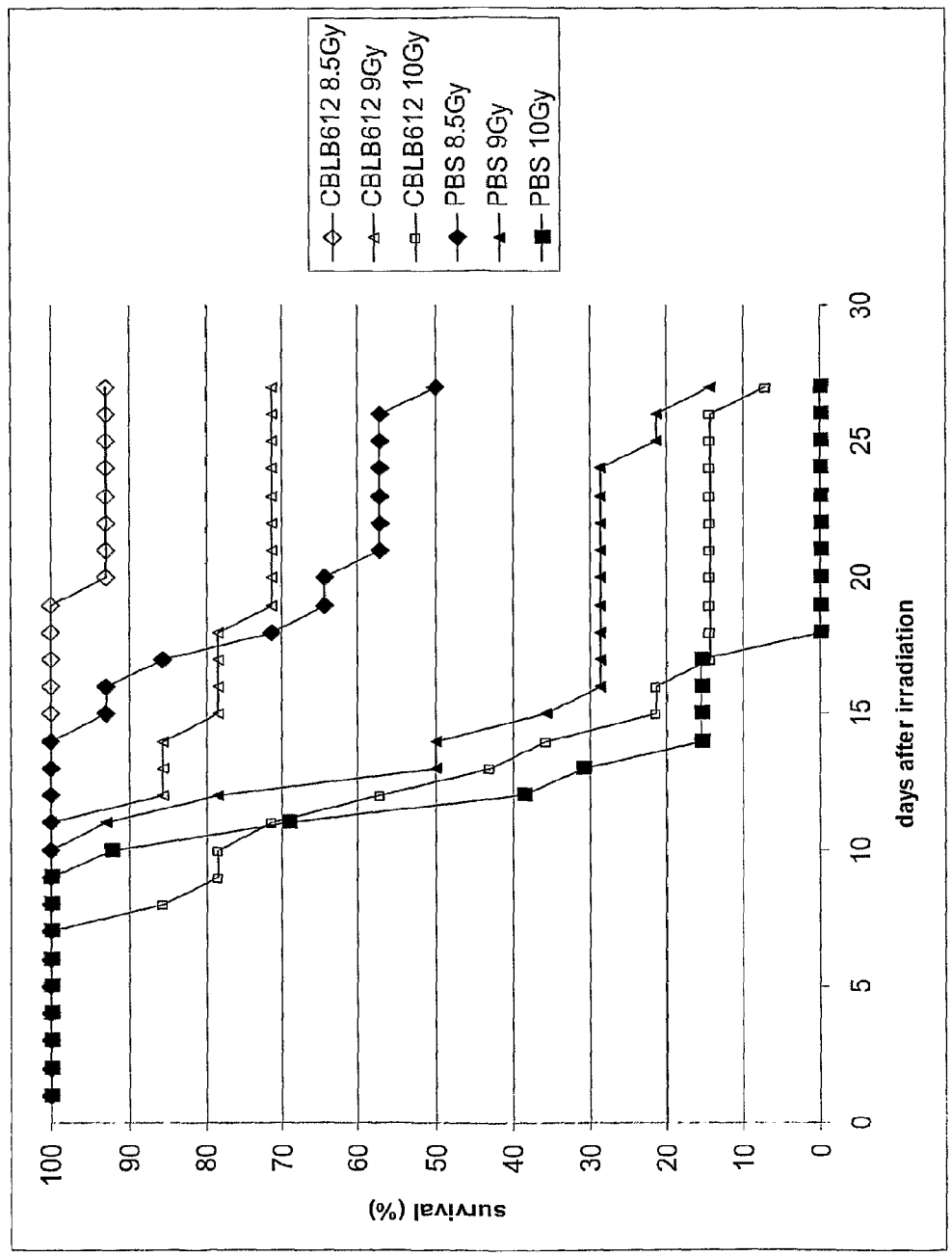
FIG. 22 illustrated the mitigative activity of CBLB612. Shown is a graph of the percent survival of mice treated with 50 µg of CBLB612/mouse or PBS 1 hr after exposure to 8.5, 9, or 10 Gy of TBI.

The ability of CBLB612 to serve as a mitigator of lower dose radiation injury was also examined. For this, 50 μg of CBLB612/mouse was injected intramuscularly 1 hr after exposure to 8.5, 9, or 10 Gy of TBI. Treatment with CBLB612 increased the survival rate at every dose of radiation (FIG. 22). For example, at 8.5 Gy, 90% of the CBLB612-treated and 50% of the PBS-treated mice survived to 27 days (p=0.03), and, at 9 Gy 70% of the CBLB612-treated and 50% of the PBS-treated mice survived to 27 days (p=0.0006). No difference was observed between CBLB612-treated and control groups at lower radiation doses due to the low control mice survival (not shown). These data indicate CBLB612 may serve as a radiation mitigator, as well as a radioprotector.

The invention claimed is:

1. A compound of the formula:

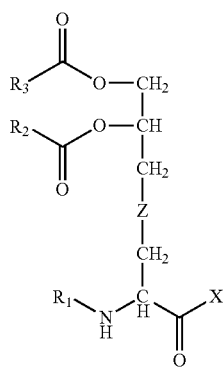

wherein, $R_1$ represents H or —CO—$R_4$, $R_2$, $R_3$ and $R_4$ independently are H or optionally substituted $C_6$-$C_{20}$ aliphatic;

X is a peptide comprising SEQ ID NO: 16; and

Z is S or $CH_2$.

2. The compound of claim 1, wherein $R_2$, $R_3$ and $R_4$ are each independently selected from the group consisting of $C_6$-$C_{20}$ alkyl, $C_6$-$C_{20}$ alkenyl, and $C_6$-$C_{20}$ alkynyl.

3. The compound of claim 2, wherein the $C_6$-$C_{20}$ alkyl is selected from the group consisting of $C_6$, $C_8$, $C_9$, $C_{10}$, $C_{12}$, $C_{14}$, and $C_{16}$.

4. The compound of claim 2, wherein the $C_6$-$C_{20}$ alkenyl is selected from the group consisting of $C_{10:1}^{D1\ trans}$, $C_{18:1}^{D9}$, and $C_{18:2}^{D9,\ 12}$.

5. The compound of claim 1, wherein $R_1$ is H and $R_2$ and $R_3$ are optionally substituted $C_{16}$ aliphatics.

6. The compound of claim 1, wherein the compound is an RR or RS stereoisomer, or mixture thereof.

7. A composition comprising the compound of claim 1 and a radioprotectant.

8. The composition of claim 7 wherein the radioprotectant is an antioxidant.

9. The composition of claim 8, wherein the antioxidant is selected from the group consisting of amifostine and vitamin E.

10. The composition of claim 7, wherein the radioprotectant is a cytokine.

11. The composition of claim 10, wherein the cytokine is stem cell factor.

12. The composition of claim 7, wherein the radioprotectant is flagellin.

13. The composition of claim 7, wherein the radioprotectant is latent TGFβ.

14. The composition of claim 7, wherein the radioprotectant is an activator of a TLR.

* * * * *